United States Patent
Rogers et al.

(10) Patent No.: US 10,183,978 B2
(45) Date of Patent: Jan. 22, 2019

(54) ANIMAL MODELS OF DUCHENNE MUSCULAR DYSTROPHY

(71) Applicant: Exemplar Genetics, LLC, Sioux Center, IA (US)

(72) Inventors: Christopher S. Rogers, North Liberty, IA (US); John R. Swart, Orange City, IA (US)

(73) Assignee: EXEMPLAR GENETICS, LLC, Sioux Center, IA (US)

( * ) Notice: Subject to any disclaimer, the term of this patent is extended or adjusted under 35 U.S.C. 154(b) by 0 days.

(21) Appl. No.: 14/164,204

(22) Filed: Jan. 26, 2014

(65) Prior Publication Data
US 2014/0223589 A1    Aug. 7, 2014

Related U.S. Application Data

(60) Provisional application No. 61/757,203, filed on Jan. 27, 2013.

(51) Int. Cl.
| | | |
|---|---|---|
| *A01K 67/00* | (2006.01) | |
| *A01K 67/027* | (2006.01) | |
| *C12N 5/00* | (2006.01) | |
| *C07K 14/47* | (2006.01) | |

(52) U.S. Cl.
CPC ...... *C07K 14/4708* (2013.01); *A01K 67/0276* (2013.01); *A01K 2217/075* (2013.01); *A01K 2227/108* (2013.01); *A01K 2267/0306* (2013.01); *C12N 2517/02* (2013.01); *C12N 2750/14143* (2013.01)

(58) Field of Classification Search
CPC .......... A01K 67/0276; A01K 2217/075; A01K 2227/108; A01K 2267/0306; C12N 2517/02
USPC ...................................... 800/9, 17; 435/325
See application file for complete search history.

(56) References Cited

U.S. PATENT DOCUMENTS

| | | |
|---|---|---|
| 7,420,099 B2 | 9/2008 | Robl et al. |
| 7,928,285 B2 | 4/2011 | Robl et al. |
| 7,989,675 B2 | 8/2011 | Welsh et al. |
| 2009/0235368 A1 | 9/2009 | Welsh et al. |
| 2009/0241203 A1 | 9/2009 | Welsh et al. |
| 2011/0197290 A1 | 8/2011 | Fahrenkrug |
| 2012/0180141 A1 | 7/2012 | Welsh et al. |
| 2012/0220037 A1 | 8/2012 | Fahrenkrug et al. |
| 2013/0203870 A1 | 8/2013 | Rogers et al. |

FOREIGN PATENT DOCUMENTS

WO    2005104835    11/2005

OTHER PUBLICATIONS

Houdebine, L-M., 2002, Journal of Biotechnology, vol. 98, p. 145-160.*
Goldman et al., 2004, Med Sci Monit, vol. 10, No. 11, RA274-285.*
Sigmund, C., Jun. 2000, Arterioscler. Thromb. Vasc. Biol., p. 1425-1429.*
Houdebine, Louis-Marie, 2007, Methods in Molecular Biology, vol. 360, p. 163-202.*
Carstea et al., 2009, World Journals of Stem Cells, vol. 1, No. 1, p. 22-29.*
Maksimenko et al., 2013, Acta Naturae, vol. 5, No. 1, p. 33-46.*
Edwards et al., 2003, American Journal of reproductive Immunology, vol. 50, p. 113-123.*
Wells et al., 2003, Trends in Biotechnology, vol. 21, No. 10, p. 428-432.*
Jang et al., 2010, Theriogenology, vol. 74, p. 1311-1320.*
Kues et al., 2011, Preventive Veterinary Medicine, vol. 102, p. 146-156.*
Araki et al., 1997, Biochemical and Biophysical research Communications, vol. 238, p. 492-497.*
Wikipedia, Ungulate, pp. 1-10.*
Selsby et al., 2015, ILAR Journal, vol. 56, No. 1, p. 116-126.*
Klymiuk et al., Jan. 7-10, 2012, Reproduction, Fertility and Development, vol. 24, No. 1, pp. 231, Abstract No. 238.*
Katinka, Feb. 11, 2012, PhD Thesis, p. 1-138.*
Altschul S.F. et al. "Basic local alignment search tool" (1990) J. Mol. Biol. 215:403-410.
Ambrosio, C.E. et al. "Ringo, a Golden Retriever Muscular Dystrophy (GRMD) dog with absent dystrophin but normal strength" (2008) Neuromuscul. Disord. 18(11):892-893.
Bordais, A. et al. "Molecular cloning and protein expression of Duchenne muscular dystrophy gene products in porcine retina" (2005) Neuromuscul. Disord. 15(7):476-87.
Bushby, K. et al. "Diagnosis and management of Duchenne muscular dystrophy, part 2: implementation of multidisciplinary care" (2010) Lancet Neurol. 9(2):177-189.
Bushby, K. et al. "Diagnosis and management of Duchenne muscular dystrophy, part 1: diagnosis, and pharmacological and psychosocial management" (2010) Lancet Neurol. 9(1):77-93.
Chapman, V.M. et al. "Recovery of induced mutations for X chromosome-linked muscular dystrophy in mice" (1989) Proc. Natl. Acad. Sci. USA 86(4):1292-1296.
Cooper, D.K. et al. "Will the pig solve the transplantation backlog?" (2002) Annu. Rev. Med. 253:133-147.
Dixon, J.A. et al. "Large Animal Models of Heart Failure, A Critical Link in the Translation of Basic Science to Clinical Practice" (2009) Circ. Heart Fail. 2(3): 262-271.
Durbeej, M. et al. "Muscular dystrophies involving the dystrophin-glycoprotein complex: an overview of current mouse models." (2002) Curr. Opin. Genet. Dev. 12(3):349-361.

(Continued)

*Primary Examiner* — Shin Lin Chen
(74) *Attorney, Agent, or Firm* — Intrexon Corporation

(57) ABSTRACT

The present invention provides transgenic, large non-human animal models of Duchenne muscular dystrophy, Becker muscular dystrophy, and DMD-associated dilated cardiomyopathy, as well as methods of using such animal models in the identification and characterization of therapies for Duchenne muscular dystrophy, Becker muscular dystrophy, and DMD-associated dilated cardiomyopathy.

7 Claims, 7 Drawing Sheets
(6 of 7 Drawing Sheet(s) Filed in Color)
Specification includes a Sequence Listing.

(56) References Cited

OTHER PUBLICATIONS

Estrada, J.L. et al. "Successful cloning of the Yucatan minipig using commercial/occidental breeds as oocyte donors and embryo recipients" (2008) Cloning Stem Cells 10(2):287-296.
Farini, A. et al. "Cell based therapy for Duchenne muscular dystrophy" (2009) J. Cell Physiol. 221(3):526-34.
Grosse-Hovest, L. et al. "Cloned transgenic farm animals produce a bispecific antibody for T cell-mediated tumor cell killing." (2004) Proc. Natl. Acad. Sci. USA 101(18):6858-6863.
Grounds, M.D. et al. "Towards developing standard operating procedures for pre-clinical testing in the mdx mouse model of Duchenne muscular dystrophy" (2008) Neurobiol. Dis. 31(1):1-19.
Guglieri, M. et al. "Molecular treatments in Duchenne muscular dystrophy" (2010) Curr. Opin. Pharmacol. 10(3):331-337.
Hastings, A.B. et al. "Comparative physiological responses to exercise stress" (1982) J. Appl. Physiol. 52(4)1077-1083.
Hao et al. "Production of endothelial nitric oxide synthase (eNOS) over-expressing piglets" (2006) Transgenic Res. 15:739-750.
Hoffman, E.P. et al. "Conservation of the Duchenne muscular dystrophy gene in mice and humans" (1987) Science 238(4825):347-350.
Hoffman, E.P. et al. "Dystrophin: the protein product of the Duchenne muscular dystrophy locus" (1987) Cell 51 (6):919-928.
Lai et al. "Generation of cloned transgenic pigs rich in omega-3 fatty acids" (2006) Nature Biotechnol. 24(4):435-436.
Lai et al. "A Method for Producing Cloned Pigs by Using Somatic Cells as Donors" (2004) Meth. Mol. Biol. 254(2):149-163.
Lai et al. "Production of cloned pigs by using somatic cells as donors" (2003) Cloning and Stem Cells 5(4):233-241.
Lai et al. "Production of alpha-1,3-galactosyltransferase knockout pigs by nuclear transfer cloning" (2002) Science 295:1089-1092.
Lai and Prather "Creating genetically modified pigs by using nuclear transfer" (2003) Rep. Biol.Endocrinol. I:82:1-6.
Li et al. "Cloned Transgenic Swine Via in Vitro Production and Cryopreservation" (2006) Biol. Reprod. 75:226-230.
Melzer, W. et al. "Malignant hyperthermia and excitation-contraction coupling" (2001) Acta Physiol. Scand. 171(3):367-378.
Meyerholz, D.K. et al. "Loss of cystic fibrosis transmembrane conductance regulator function produces abnormalities in tracheal development in neonatal pigs and young children" (2010) Am. J. Respir. Crit. Care Med. 182(10):1251-1261.
Meyerholz, D.K. et al. "Pathology of gastrointestinal organs in a porcine model of cystic fibrosis" (2010) Am. J. Pathol. 176(3):1377-1389.
Panepinto, L.M. et al. "The Yucatan miniature pig: characterization and utilization in biomedical research" (1986) Lab. Anim. Sci. 36(4):344-347.
Park et al. "Production of nuclear transfer-derived swine that express the enhanced green fluorescent protein" (2001) Animal Biotechnol. 12(2):173-181.
Park et al. "Developmental potential of porcine nuclear transfer embryos derived from transgenic fetal fibroblasts infected with the gene for the green fluorescent protein: comparison of different fusion/activation conditions." (2001) Biol. Reprod. 65:1681-1685.
Piedrahita, J.A. "Targeted modification of the domestic animal genome" (2000) Theriogenol. 53(1):105-116.
Rogers, C.S. et al. "Production of CFTR-null and CFTR-DeltaF508 heterozygous pigs by adeno-associated virus-mediated gene targeting and somatic cell nuclear transfer" (2008) J. Clin. Invest. 118(4):1571-1577.
Rogers, C.S. et al. "Disruption of the CFTR gene produces a model of cystic fibrosis in newborn pigs" (2008) Science 321(5897):1837-1841.
Rogers, C.S. et al. "The porcine lung as a potential model for cystic fibrosis" (2008) Am. J. Physiol. Lung Cell. Mol. Physiol. 295(2):L240-263.
Russell, D.W. et al. "Human gene targeting by viral vectors" (1998) Nat. Genet. 18(4):325-330.
Schatzberg, S. J. et al. "Molecular analysis of a spontaneous dystrophin 'knockout' dog" (1999) Neuromuscul. Disord. 9(5):289-295.
Shimatsu, Y. et al. "Canine X-linked muscular dystrophy in Japan (CXMDJ)" (2003) Exp. Anim. 52(2):93-97.
Stoltz, D.A. et al. "Cystic fibrosis pigs develop lung disease and exhibit defective bacterial eradication at birth" (2010) Sci. Transl. Med. 2(29): 29ra31.
Tatusova, Ta et al. "Blast 2 Sequences, a new tool for comparing protein and nucleotide sequences" (1999) FEMS . Microbial. Lett. 174: 247-250.
Trollet, C. et al. "Gene therapy for muscular dystrophy: current progress and future prospects" (2009) Exp. Opin. Biol. Ther. 9(7):849-866.
Valentine, B.A. et al. "Canine X-linked muscular dystrophy as an animal model of Duchenne muscular dystrophy: a review" (1992) Am. J. Med. Genet. 42(3):352-356.
Vasquez, K.M. et al. "Manipulating the mammalian genome by homologous recombination" (2001) Proc. Natl. Acad. Sci. USA 98(15):8403-8410.
Wallace, G.Q. et al. "Mechanisms of muscle degeneration, regeneration, and repair in the muscular dystrophies" (2009) Annu. Rev. Physiol. 71:37-57.
Wang, Z. et al. "Gene therapy in large animal models of muscular dystrophy" (2009) ILAR J. 50(2):187-98.
Watchko, J.F. et al. "Functional characteristics of dystrophic skeletal muscle: insights from animal models" (2002) J. Appl. Physiol. 93(2):407-417.
Yokota, T. et al. "Efficacy of systemic morpholino exon-skipping in Duchenne dystrophy dogs" (2009) Ann. Neurol. 65(6):667-676.
Yokota, T. et al. "Potential of oligonucleotide-mediated exon-skipping therapy for Duchenne muscular dystrophy" (2007) Exp. Opin. Biol. Ther. 7(6):831-42.
WO 2014/117045 International Search Report dated May 5, 2014.
GenBank: CU582789.7 Pig DNA sequence from clone CH242-9G1 1on chromosome X, complete sequence. Aug. 16, 2012. [Retrieved from the Internet Jun. 5, 2014: <http://www.ncbi.nlm.nih.gov/nuccore/340805675>]; nucleotides 109672-1 11075 and 111216-1112618.
GenBank: AF335420.3. Cloning vector pPGKneo-ll, complete sequence. Jul. 25, 2002. [Retrieved from the Internet Jun. 5, 2014: <http://www.ncbi.nlm.nih.gov/nuccore/AF335420>]; Nucleotides 284-1978.
Burkhardt. "Generation of a tailored pig model of Duchenne Muscular Dystrophy" Ph.D. Thesis (2012) [Retrieved from the Internet Apr. 8, 2014 http://edoc.ub.unimuenchen.de/14243/1Burkhardt_Katinka.pdf] p. 6-7; p. 78, Figure IV.14, and its legend; p. 75, section 3.2.3; p. 76, last para; p. 79, 1st para, p. 88; p. 85, Figure IV.19 and its legend.
Kim, M.H. et al. "Myogenic Akt signaling attenuates muscular degeneration, promotes myofiber regeneration and improves muscle function in dystrophin-deficient mdx mice" (2011) Hum. Mol. Genet. 20(7):1324-1338.

\* cited by examiner

ANIMAL MODELS OF DUCHENNE MUSCULAR DYSTROPHY

CROSS REFERENCE TO RELATED APPLICATIONS

This application claims priority to U.S. Provisional Application No. 61/757,203, filed Jan. 27, 2013, and to PCT Appln. No. PCT/US14/13083, filed concurrently herewith, each of which is hereby incorporated by reference in their entireties.

STATEMENT AS TO FEDERALLY SPONSORED RESEARCH

This invention was made with government support under grant number AR061900 awarded by the National Institutes of Health and the National Heart, Lung and Blood Institute. The government has certain rights to this invention.

SEQUENCE LISTING

The instant application contains a Sequence Listing which has been submitted in ASCII format via EFS-Web and is hereby incorporated by reference in its entirety. Said ASCII copy, created on Jan. 23, 2013, is named EXEM0007.txt and is 6,788 bytes in size.

FIELD OF THE INVENTION

This invention relates to transgenic, non-human animal models of disease, cells that can be used to make such animals, and methods of using these animals and cells.

BACKGROUND OF THE INVENTION

Many human diseases and conditions are caused by gene mutations. Substantial effort has been directed towards the creation of transgenic animal models of such diseases and conditions to facilitate the testing of approaches to treatment, as well as to gain a better understanding of disease pathology. Early transgenic animal technology focused on the mouse, while more recent efforts, which have been bolstered by the development of somatic cell nuclear transfer (SCNT), have included larger animals, including pigs, cows, and goats. This technology has resulted in the production of, for example, pigs in which the gene encoding α-1,3-galactosyltransferase has been knocked out, in efforts to generate organs that can be used in xenotransplantation (see, e.g., Lai et al., Science 295:1089-1092, 2002). Further, this technology has resulted in the production of CFTR−/− and CFTR-ΔF508/ΔF508 pigs (see, e.g., U.S. Pat. No. 7,989,675 and U.S. patent application Ser. No. 12/283,980); and LDLR+/− and LDLD −/− pigs (see, e.g., U.S. patent application Ser. No. 13/368,312). Additional applications of this technology include the production of large quantities of human proteins (e.g., therapeutic antibodies; see, e.g., Grosse-Hovest et al., Proc. Natl. Acad. Sci. U.S.A. 101(18): 6858-6863, 2004). Substantial benefits may be obtained by the use of somatic cell nuclear transfer technology in the production of large animal models of human disease.

One example of a condition caused in part by a genetic mutation is Duchenne muscular dystrophy (DMD). DMD is a progressive neuromuscular disease caused by mutations in the X-linked dystrophin gene (DMD), which encodes the protein dystrophin (Hoffman, E. P., et al.; Cell 1987, 51 (6), 919-28). DMD is the most common muscular dystrophy, affecting approximately 1 in 3500 male births. DMD patients experience progressive weakness and degeneration in skeletal muscle, including the diaphragm, cardiac muscle, and some smooth muscle (Wallace, G. Q., et al. Annu Rev Physiol 2009, 71, 37-57).

Symptoms of DMD usually appear in male children before age five, but may appear in infancy. Progressive proximal muscle weakness of the legs and pelvis from loss of muscle mass is observed first, which spreads to the arms, neck, and other areas. Early signs may include pseudohypertrophy, low endurance, and difficulties in standing. As the condition progresses, muscle tissue experiences wasting and eventually undergoes fibrosis. By age 10, braces are usually required to aid in walking, with most patients becoming wheelchair dependent by age 12. Later symptoms may include abnormal bone development that lead to skeletal deformities, including curvature of the spine. Due to progressive deterioration of muscle, loss of movement occurs eventually leading to paralysis. The average life expectancy for patients afflicted with DMD is around 25 years.

There is no current cure for DMD. Current treatments include steroids, physical therapy, orthopedic appliances, and respiratory support, however none are directed at the underlying mechanistic defect. See Bushby, K.; et al.; Lancet Neurol 2010, 9 (2), 177-89; Bushby, K, et al.; Lancet Neurol 2010, 9 (1), 77-93. While these interventions have improved the lives of patients, DMD remains a lethal disease.

New gene- and cell-based therapies for DMD along with systemic delivery systems are rapidly advancing, however moving these therapeutic approaches to the clinic has been hampered by the lack of appropriate model systems. The available rodent models for DMD are not well suited for these applications due to their failure to develop an appropriate phenotype, and the naturally occurring canine models are problematic because of a wide variability in phenotype, limited choice of mutations, significant cost, and social acceptance concerns. Therapeutic strategies that have shown promise in these models have yet to be successfully translated to patients. An animal model that accurately and consistently replicates the clinical phenotype of human DMD and shares similarities to humans in size, anatomy, physiology, and genetics would be a transformative resource in bridging the substantial gap between models currently used for early-stage drug discovery and human clinical trials. In one embodiment, the present invention provides a new model of DMD in large, non-human mammals, for example, porcine. A successful large, non-human animal model that accurately replicates the manifestations of human DMD, and shares similarities to humans in size, anatomy, physiology, and genetics (for example, a porcine model) would have broad applicability and be a transformative resource in the DMD research community, and also provide the ability to develop much-needed models of other muscular dystrophies.

Furthermore, there is great interest in advancing medical devices, interventional strategies, and non-invasive diagnostic methods beyond their current state, but these fields are also limited by the current model systems. Rodent models are not well suited for most of these applications due to their size. Therefore, in one aspect of the invention, the transgenic animal model is a new model for DMD in a miniature pig breed. In one embodiment, the present invention accomplishes this in two steps by combining gene targeting and SCNT.

SUMMARY OF THE INVENTION

The invention provides large, non-human animal models of human diseases or conditions, in which one or more genes associated with the diseases or conditions include one or more targeted mutations. The animals of the invention can be, for example, ungulates such as pigs, cows, sheep, and goats. In one example, the disease or condition is Duchenne muscular dystrophy, Becker muscular dystrophy, or DMD-associated dilated cardiomyopathy and the gene including one or more mutations is the dystrophin (DMD) gene.

The animal models of the invention can include the mutation(s) in one or both alleles of the DMD gene in the genome of the transgenic animal, and the mutation(s) can result in full or partial inactivation of the gene. In one example, the mutation includes an insertion of an exogenous nucleic acid molecule and/or a transcription/translation termination sequence. In another example, the mutation includes a deletion of an endogenous nucleic acid molecule or a portion thereof. In yet another example, the mutation substantially eliminates expression of a functional gene product of the targeted gene in cells in which such expression normally takes place, absent the mutation.

In one example, the animal is a male and the mutation is on the X-chromosome. In another example, the animal is a female and the mutation is on one or both of the X-chromosomes. In the case of an animal with a mutation or mutations in both alleles of a gene, the mutation or mutations in each allele can be identical to one another or can be different.

The animal models of the invention may also include a homologous transgenic copy of a wild-type or mutated gene from a different animal. In one embodiment, the invention may include an orthologous gene from a different animal. The animal models may thus include, for example, in addition to a mutation/inactivation of an endogenous gene, an inserted copy of a corresponding gene from another species. Thus, for example, an animal (such as a pig) in which an endogenous DMD gene is mutated or inactivated may be modified to include a DMD gene from another animal (such as a human), which may be wild-type or may include a mutation. The invention therefore provides transgenic, large (non-human) animal models of human diseases and conditions (e.g., pigs) in which one or more endogenous genes associated with the disease or condition are knocked-out (i.e., genetically altered in such a way as to inhibit the production or function of the product or gene) and replaced with a homologous wild-type or mutated gene derived from a different animal (e.g., a human). In one example, a pig with its endogenous porcine DMD gene knocked-out expresses a human transgene encoding the DMD gene or a mutation thereof.

The invention also provides isolated cells of transgenic, large non-human animal models of human diseases or conditions, in which one or more genes associated with the diseases or conditions include one or more targeted mutations. The animals can be, for example, ungulates, such as, e.g., pigs, cows, sheep, and goats. In one example, the disease or condition is Duchenne muscular dystrophy, Becker muscular dystrophy, or DMD-associated dilated cardiomyopathy and the gene including one or more mutations is the DMD gene.

Examples of DMD mutations that can be included in the animals and cells of the present invention can include mutations affecting the synthesis of dystrophin (for example, mutations that prevent any functional dystrophin from being produced), and mutations that give rise to the production of an abnormal version of dystrophin that retains some function (for example, as seen in Becker muscular dystrophy and DMD-associated dilated cardiomyopathy).

The cells of the invention can include the mutation(s) in one or both alleles (as in a female, non-human mammal in the case of DMD) of the genes in the genomes of the cells, and the mutation(s) can result in full or partial inactivation of the gene(s). In one example, the mutation includes an insertion of an exogenous nucleic acid molecule and/or a transcription/translation termination sequence. In another example, the mutation substantially eliminates expression of a functional gene product of the targeted gene in cells in which such expression normally takes place, absent the mutation. In the case of a cell with a mutation or mutations in both alleles of a gene, the mutation or mutations in each allele can be identical to one another or can be different. In one example, the cells are fetal cells, such as fetal fibroblasts. Additional examples of cell types included in the invention are provided below.

The invention further provides methods of making transgenic, large non-human animal models of diseases or conditions as described above and elsewhere herein. The methods can include the steps of: (i) introducing one or more mutations into an allele of one or more genes associated with a disease or condition in a cell (e.g., a fetal fibroblast) to generate a donor cell; (ii) introducing the nucleus of the donor cell into a recipient cell (e.g., an enucleated oocyte) to generate an embryo; and (iii) transferring the embryo into a surrogate female. The animals can be, for example, ungulates, such as, e.g., pigs, cows, sheep, and goats. In one example, the disease or condition is DMD and the gene including one or more mutations is a DMD gene. In a variation of these methods, the donor cell includes one or more mutations in one allele of a gene located on the X-chromosome, such as DMD. In another variation of these methods, the donor cell includes one or more mutations in one allele of a gene located on the X-chromosome, and the method is carried out to introduce one or more mutations into the other allele on the other X-chromosome (for example, in a female model with respect to DMD). In another example, the methods further involve breeding an animal that is born from the surrogate female to obtain a male mutant that exhibits symptoms of DMD.

The invention also includes methods of identifying therapeutic agents that can be used in the treatment of diseases or conditions (e.g., the diseases of Duchenne muscular dystrophy, Becker muscular dystrophy, or DMD-associated dilated cardiomyopathy). These methods involve administering one or more candidate therapeutic agents to a transgenic animal, as described above, and monitoring the animal for one or more symptoms of the disease or condition. Detection of improvement or other change in a symptom of the disease or condition indicates the identification of a compound that may be used in the treatment or prevention of the disease or condition.

The invention also includes methods of providing surgical training and medical imaging that can be used in the treatment of diseases or conditions (e.g., Duchenne muscular dystrophy, Becker muscular dystrophy, or DMD-associated dilated cardiomyopathy). These methods involve using the transgenic animals of the present invention for the refinement of surgical techniques using standard approaches, as well as minimally invasive and robotic technologies. In the context of medical imaging, new and improved technologies including noninvasive imaging could be evaluated using instrumentation designed for humans.

The invention further provides methods of targeting the introduction of mutations into pig cells. These methods involve the steps of providing pig cells (e.g., fetal fibroblasts), using an adeno-associated viral vector to deliver a gene targeting construct to the isolated pig cells, in the absence of cell detachment and reattachment, and selecting gene-targeted clones. The cells are in culture for 30 days or less (e.g., 20 days or less in the Examples) during the targeting construct delivery and selection steps. These methods can be used, for example, for the introduction of a mutation into a dystrophin gene in the pig cell. Information concerning other examples of mutations that can be used in the present invention, as well as the use of the present methods to inactivate or replace genes (e.g., to replace pig genes with human genes), is provided below.

By "donor cell" is meant a cell from which a nucleus or chromatin material is derived, for use in nuclear transfer. As is discussed elsewhere herein, nuclear transfer can involve transfer of a nucleus or chromatin only, as isolated from a donor cell, or transfer of an entire donor cell including such a nucleus or chromatin material.

By "genetic modification," "mutation," or "disruption" of a gene (e.g., a DMD gene) is meant one or more alterations in gene sequences (including coding sequences and non-coding sequences, such as introns, promoter sequences, and 5' and 3'-untranslated sequences) that alter the expression or activity of this gene by, for example, insertion (of, e.g., heterologous sequences, such as selectable markers, and/or termination signals), deletion, frame shift mutation, silent mutation, nonsense mutation, missense mutation, point mutation, or combinations thereof. In one example, the amino acid sequence encoded by the nucleic acid sequence has at least one amino acid altered as compared to a naturally-occurring sequence. Examples of mutations include the insertion of a polynucleotide into a gene, the deletion of one or more nucleotides from a gene, and the introduction of one or more base substitutions into a gene. In one embodiment of the present invention, modifications of DMD gene sequences are those that lead to one or more features or symptoms of Duchenne muscular dystrophy, Becker muscular dystrophy, or DMD-associated dilated cardiomyopathy in transgenic animals including a mutation in, or disruption of, one of the DMD alleles. In another embodiment of the present invention, modifications of DMD gene sequences are those that lead to one or more features or symptoms of Duchenne muscular dystrophy, Becker muscular dystrophy, or DMD-associated dilated cardiomyopathy in transgenic animals including a mutation in, or disruption of, both DMD alleles. As is discussed elsewhere herein, the modifications in the two DMD alleles of such animals can be identical or different. Further, the modifications can result in a complete lack of functional dystrophin production, or can result in diminished functional dystrophin production, as may be characteristic of less severe forms of the disease such as Becker muscular dystrophy, or DMD-associated dilated cardiomyopathy.

Examples of such mutations include any such mutations known in the art, for example, those listed at www.dmd.nl/database.html or www.umd.be/DMD/W_DMD/index.html.

In one example, a mutation is introduced by the insertion of a polynucleotide (for example, a positive selection marker, such as an antibiotic resistance gene (e.g., a neomycin resistance gene)) into an endogenous gene. Optionally, a mutation that is introduced into such an endogenous gene reduces the expression of the gene. If desired, the polynucleotide may also contain recombinase sites flanking the positive selection marker, such as loxP sites, so that the positive selection marker may be removed by a recombinase (e.g., cre recombinase).

By "homologous" genes is meant a pair of genes from two animal species that encode proteins having similar functional and physical properties. The proteins encoded by homologous genes are often very similar in structure and function (although not always), and typically have a common evolutionary origin. In one embodiment, the sequence identity is typically equal to or greater than 80%, equal to or greater than 90%, equal to or greater than 95%, or equal to or greater than 98% between two gene homologs. One example of a homologous gene pair is the porcine DMD and human DMD gene locus.

By "orthologous" genes or "orthologs" is meant genes that are separated by a speciation event wherein one ortholog may be substituted by genetic engineering into its corresponding gene in another species.

By animal "knock-out" is meant an animal (for example, a pig or mouse; also see other animals described herein) having a genome in which the function of a gene has been disrupted, or "knocked-out." A common method of producing disabled genes using recombinant DNA technology involves inserting an antibiotic resistance gene into the normal DNA sequence of a clone of the gene of interest by homologous recombination. This disrupts the action of the gene, thereby preventing it from leading to the production of an active protein product. A cell (or cell nucleus) in which this transfer is successful can be injected into a recipient cell (e.g., an enucleated oocyte) to generate a transgenic animal by nuclear transfer. In another approach, the cell is injected into an animal embryo, producing a chimeric animal. These animals may be bred to yield a strain in which all of the cells contain the knocked-out gene.

By "heterozygous knock-out non-human mammal" is meant a mammal other than a human in which one of the two alleles of an endogenous gene (such as the DMD gene) have been genetically targeted, or knocked out, resulting in a marked reduction or elimination of expression of a functional gene product, which is achieved by gene deletion or disruption.

By "homozygous knock-out non-human mammal" is meant a mammal other than a human in which the two alleles of an endogenous gene (such as the DMD gene) have been genetically targeted, or knocked out, resulting in a marked reduction or elimination of expression of a functional gene product, which is achieved by gene deletion or disruption. According to the invention, the genetic targeting event at both alleles may or may not be the same. Thus, a non-human animal, in which the two alleles of an endogenous gene (such as a DMD gene) have been genetically targeted by two different targeting vectors resulting in the null expression of the gene, would be considered as being a homozygous knock-out non-human mammal.

An example of a "knock-in mutation" is one resulting in the insertion of a mutation into an endogenous gene.

By "recipient cell" is meant a cell into which a donor cell, a donor cell nucleus, or donor cell chromatin is introduced. In one preferred embodiment, recipient cells are enucleated prior to nuclear transfer. Examples of recipient cells include oocytes, fertilized zygotes, and two-cell embryos.

By "transgenic, large non-human animal" is meant any non-human animal that includes a genetic modification, as defined herein. Examples of such animals include animals other than mice such as, for example, ungulates. Examples of ungulates that can be used in the invention include members of the orders Perissodactyla and Artiodactyla, such as any members of the family Suidae, and in particular any member of the genus *Sus*, such as *Sus scrofa*, which is also known as the domestic pig or a subspecies thereof (*Sus scrofa domestica*). Examples of *Sus scrofa domestica* breeds that can be used in the present invention include Landrace, Hampshire, Duroc, Chinese Meishan, Berkshire, Pietrain and Yorkshire. Examples of miniature pigs that can be used in the present invention include Ossabaw, Hanford, Sinclair, Libechov, Goettingen, Yucatan, Bama Xiang Zhu, Wuzhishan, and Xi Shuang Banna. In addition to porcines, additional ungulates that can be used in the invention include bovines, ovines, and caprines. Thus, for example, the invention can include the use of cows (e.g., Bos taurus or Bos indicus), sheep, goats, buffalos, antelopes, oxen, horses, donkeys, mule, deer, elk, caribou, water buffalo, camels, llama, alpaca, and elephants.

The invention provides several advantages over the state of the art, as it provides large, non-human animal models that can be used in the identification and characterization of therapies for genetic diseases, for example, the present invention describes the development of the first gene-targeted large animal model of a human neuromuscular disease. One example of such a disease is DMD, which, as discussed above, is a devastating disease, leading to deterioration of muscle, loss of movement, paralysis, and, eventually, premature death.

Several murine models of DMD are currently available and widely studied. While they have been extremely useful for understanding some aspects of disease pathogenesis and piloting new therapeutic strategies, they fail to recreate the muscle weakness phenotype that is so devastating in the human disease (See, e.g., Durbeej, M., et al. Curr Opin Genet Dev 2002, 12 (3), 349-61; Hoffman, E. P., et al. Science 1987, 238 (4825), 347-50; Chapman, V. M., et al. Proc Natl Acad Sci USA 1989, 86 (4), 1292-6; Grounds, M. D., et al. Neurobiol Dis 2008, 31 (1), 1-19). Canine models of DMD, particularly the dystrophin-deficient Golden Retriever (GRMD) possess many of the clinical manifestations seen in patients including progressive muscle weakness, fibrosis, joint contractures, and eventual death from cardiac and respiratory failure (see, e.g., Schatzberg, S. J., et al. Neuromuscul Disord 1999, 9 (5), 289-95; Shimatsu, Y., et al. Exp Anim 2003, 52 (2), 93-7; Valentine, B. A., et al. Am J Med Genet 1992, 42 (3), 352-6). However, there is an inexplicable variability in disease severity among GRMD animals, with some having an extremely mild phenotype (see, e.g., Ambrosio, C. E., et al. Neuromuscul Disord 2008, 18 (11), 892-3; Watchko, J. F., et al. J Appl Physiol 2002, 93 (2), 407-17). This "leaky" and inconsistent phenotype makes it difficult to interpret therapeutic interventions. Furthermore, an unpredictable disease penetrance hinders effective breeding programs. Because the dog is a common companion animal, social acceptance and the emotional attachment of the researcher provide logistical and workplace challenges that can also be extremely expensive.

A porcine model offers several advantages over the canine models. First, gene targeting provides an opportunity to introduce almost any desired mutation. This will allow for the targeting of "hotspot" regions that represent a broader range of patient-specific mutations. Second, somatic cell nuclear transfer (SCNT), sometimes referred to as cloning, offers the unique ability to produce genetically identical DMD pigs, as well as genetically identical control animals (with the exception of the specific mutation of interest). This will reduce phenotypic variability and allow researchers to study specific mechanisms and treatments without concern of extraneous genetic factors. Conversely, the wide range of pig breeds also allows for genetic outcrossing as a means to identify and study modifier genes. By comparison, the canine models are limited to a few naturally occurring mutations, potentially restricting the usefulness of therapies developed in the dogs. Furthermore, gene targeting has not been reported in dogs, and canine SCNT is extremely inefficient and not currently performed in the United States (see, e.g., Jang, G.; Kim, et al. Theriogenology 2010, 74 (8), 1311-20). Finally, because of the longstanding role of pigs in human food production, their use in biomedical research has better social acceptance and lower costs of production and housing than dogs.

Availability of DMD animal models, for example, pig models, will allow investigators to address key problems that have persisted unresolved for years. As a result, it will be possible to develop new treatments, medical devices, therapies, and preventions for DMD. Further, given the close physiological relationship between humans and large animals, such as pigs, there is an increased likelihood that results obtained using the animal models of the invention can be applied to humans, relative to other animal models. For example, the commonly used mouse models of DMD fail to recreate the muscle weakness phenotype seen in human DMD. This is likely due to genetic, biochemical, and physiological differences between mice and humans. Specifically with respect to pigs, it is noted that pigs and humans have anatomical, histological, biochemical, and physiologic similarities.

The invention thus can be used to provide substantial benefits in the treatment of diseases and conditions caused by or associated with gene mutations, such as DMD. Other features and advantages of the invention will be apparent from the drawings, the detailed description, the experimental examples, and the claims.

BRIEF DESCRIPTION OF THE DRAWINGS

This patent application file contains at least one drawing executed in color. Copies of this patent application publication with color drawing(s) will be provided by the Office upon request and payment of the necessary fee.

FIG. 3A shows a representative 96-well gel containing a PCR-positive clone (boxed in red). The other wells represent $Neo^R$ clones resulting from random integration, or in the case of lighter bands, leftover DNA from dead cells. Each PCR-positive clone was re-electrophoresed on a conventional agarose gel to confirm proper size, as shown, for example, in FIG. 3B. Expected sizes were 1.9 kb for wild-type DMD and 3.6 kb for targeted DMD. Lanes 1-3 represent 3 different DMD$^{ex52del}$ male cell colonies. Lane 1 is from a monoclonal colony, whereas lanes 2 and 3 represent polyclonal colonies. Lanes 4-6 represent DMD$^{ex52del/+}$ female cells (the smaller wild-type PCR product is more intense, in part, because of a higher PCR efficiency). FIG. 3C shows two sequence chromatograms (SEQ ID NOS 2 and 3, respectively, in order of appearance) of the site of DMD exon 52 deletion and replacement by the Neo$^R$ cassette.

FIG. 4A shows a Southern blot of DMD$^{ex52del}$ fetal genomic DNA hybridized with a DMD-specific probe and FIG. 4B shows a Southern blot of DMD$^{ex52del}$ fetal genomic DNA hybridized with a Neo$^R$-specific probe. MfeI-digested genomic DNA was hybridized with a probe that detects porcine DMD downstream of the targeting vector boundary. The DMD-targeted allele (FIG. 4A) produced an approximately 6.3 kb band, and the wild-type band is approximately 4.7 kb. The same DNA was hybridized with a probe that detects the Neo$^R$ cassette (FIG. 4B), yielding only the targeted 6.3 kb band. Lanes 1-6 contain DNA from individual DMD$^{ex52del}$ male fetuses. Lane WT contains genomic DNA from a wild-type pig.

FIG. 5A is a photograph of two DMD pigs at 15 weeks of age. FIG. 5B shows PCR genotyping for DMD-targeted pigs. Lane 1 represents a wild-type pig, and lanes 2-7 are from DMD pigs produced in the initial litters. The asterisk indicates a pig from which the Neo$^R$ cassette was successfully excised. Cells were obtained from newborn pigs and will be used to produce additional Neo$^R$-excised DMD pigs. FIG. 5C is a genomic Southern blot for DMD-targeted pigs. DNA was hybridized with a probe against DMD (upper) or Neo$^R$ (lower). Lane 1 represents a wild-type pig, and lanes 2-4 are DMD pigs. FIG. 5D is a graph showing Creatine kinase measurements from wild-type (n=3) and DMD pigs (n=4). Error bars indicate SEM. FIG. 5E is a Western blot of skeletal and cardiac muscle in a DMD pig and a wild-type pig. TA, tibialis anterior; GAS, gastrocnemius; DIA, diaphragm; LV, left ventricle, and RV, right ventricle.

DETAILED DESCRIPTION OF THE INVENTION

The invention provides animal models of human disease (e.g., DMD), which can be used in the identification and characterization of approaches for treating the diseases and conditions. As is discussed further below, the animal models of the invention are large, non-human animals, such as pigs, which have been genetically modified to include one or more mutations in a gene associated with a particular disease or condition, for example, the dystrophin gene, which is located on the X chromosome. The genetic modifications can result in the animals having one or more symptoms characteristic of the disease or condition. Animals exhibiting such symptoms are particularly advantageous in the development of therapeutic approaches, as candidate drugs and other approaches to treatment can be evaluated for effects on the symptoms in such animals. Thus, in addition to the animal models themselves, the invention also provides methods of using the animals for identifying and characterizing treatments.

Further, the invention includes methods of making transgenic, large non-human animal models and cells that can be used in these methods. The animal models systems, methods, and cells of the invention are described further, below.

In one embodiment, the invention provides a heterozygous or homozygous knock-out non-human mammal (e.g., a pig). In one example, the invention provides a male pig with its endogenous porcine DMD gene knocked-out (i.e., a DMD– pig.)

In addition to animals including knock-outs or mutations in endogenous genes, the invention also includes transgenic, large non-human animal models of human diseases and conditions (e.g., pigs), in which one or more endogenous genes associated with the diseases or conditions are knocked-out (i.e., genetically altered in such way as to inhibit the production or function of the products of these genes) and replaced with a comparable wild-type or mutated gene derived from a different animal (e.g., a human). In one example, a pig with its endogenous porcine DMD gene knocked-out, expresses a mutant human DMD transgene. Alternatively, the human transgene may encode a normal, wild-type copy of a gene of interest (e.g., DMD). These embodiments of the invention are especially useful for the generation of non-human animal models of human diseases and conditions that can be used to test existing and potential therapeutics that may only (or may preferentially) modulate or treat the disease when contacting, or being in the presence of, human copies of the disease gene or protein in question.

The invention is described herein in reference to animal models of Duchenne muscular dystrophy, Becker muscular dystrophy, or DMD-associated dilated cardiomyopathy, which are generated by mutation, deletion or replacement of the DMD gene. However, the methods of the invention are also applicable to the development of animal models of additional diseases and conditions.

Figure 1:
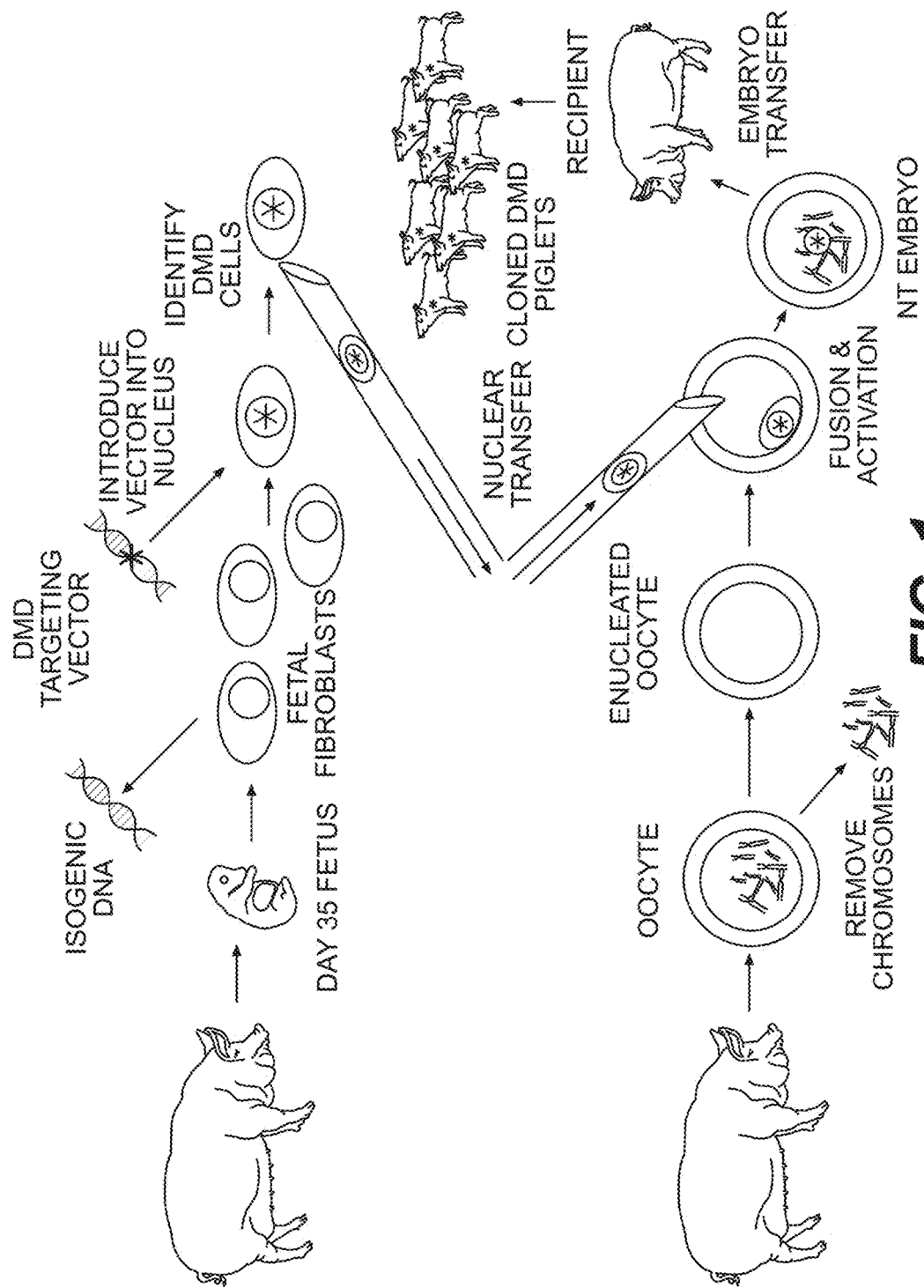
FIG. 1 is a schematic drawing showing one example of a method for generating DMD-targeted pigs. Fibroblasts are obtained from day 35 Yucatan fetuses. The targeting vector (with, for example, a DMD mutation indicated by the asterisk) is introduced to fetal fibroblasts via rAAV infection. In one example, the DMD mutation is a $DMD^{ex52del}$ mutation (i.e., the deletion of exon 52, as described in Example 2). Properly targeted cells are identified by PCR and Southern blot. Following nuclear transfer and fusion and/or activation, nuclear transfer embryos are transferred to recipient animals. After a 114 day gestation period, the resulting piglets have one DMD-targeted allele.

The transgenic animals of the invention can be made using the following general strategy, which combines gene targeting and somatic cell nuclear transfer (SCNT), also known as cloning. Briefly, the genome of a cell (e.g., a fetal fibroblast) from an animal of interest, such as a pig, is genetically modified by, for example, gene targeting by homologous recombination, to create a "donor cell." According to the methods of the invention, the genetic modification results in at least partial inactivation of a gene associated with a particular disease or condition (e.g., a DMD gene in Duchenne muscular dystrophy, Becker muscular dystrophy, or DMD-associated dilated cardiomyopathy), as will be described in further detail below. The nucleus of such a genetically modified donor cell (or the entire donor cell, including the nucleus) is then transferred into a so-called "recipient cell," such as an enucleated oocyte. After activation and, typically, a brief period of in vitro culture, the resulting embryo is implanted into a surrogate female in which development of the embryo proceeds. This approach is illustrated with respect to pigs in FIG. 1. Typically, the donor cell, oocyte, and surrogate female are of the same species, but the sources can be different species, as is known in the art.

Similar procedures have been used to develop two different gene-targeted porcine models of cystic fibrosis, and a model of atherosclerosis. See, e.g., Rogers, C. S., et al. J Clin Invest 2008, 118 (4), 1571-7; Rogers, C. S., et al. Science 2008, 321 (5897), 1837-41; U.S. Pat. No. 7,989,675; U.S. patent application Ser. Nos. 13/288,720, 13/368,312 and 13/624,967.

Details of methods for making large genetically modified animals according to the invention are provided below. Additional information concerning methods for making genetically modified pigs and other large animals is known in the art and can also be used in the present invention (see, e.g., U.S. Pat. No. 7,547,816; and WO 2005/104835; Prather et al., Reproductive Biology and Endocrinology 1:82, 1-6, 2003; Hao et al., Transgenic Res. 15:739-750, 2006; Li et al., Biology of Reproduction 75:226-230, 2006; Lai et al., Nature Biotechnology 24(4):435-436, 2006; Lai et al., Methods in Molecular Biology 254(2):149-163, 2004; Lai et al., Cloning and Stem Cells 5(4):233-241, 2003; Park et al., Animal Biotechnology 12(2):173-181, 2001; Lai et al., Science 295:1089-1092, 2002; Park et al., Biology of Reproduction 65:1681-1685, 2001).

The transgenic animals of the invention can be any non-human mammals, including, for example, ungulates. Examples of ungulates that can be used in the invention include members of the orders Perissodactyla and Artiodactyla, such as any members of the family Suidae, and in particular any member of the genus Sus, such as Sus scrofa, which is also known as the domestic pig or a subspecies thereof (Sus scrofa domestica). In one example, the animal is a Yucatan miniature swine. In addition to porcines, additional ungulates that can be used in the invention include bovines, ovines, and caprines. Thus, for example, the invention can include the use of cows (e.g., Bos taurus or Bos indicus), sheep, goats, buffalos, antelopes, oxen, horses, donkeys, mule, deer, elk, caribou, water buffalo, camels, llama, alpaca, and elephants.

In one embodiment of the present invention, the transgenic animal is a pig. Pigs share many similarities with humans including anatomy, biochemistry, physiology, size (particularly miniature pig breeds), lifespan, and genetics. The pig has proven to be an excellent model for obesity, diabetes, alcoholism, hypertension, skin physiology, intestinal function, nutrition, and injury (see, e.g., Rogers, C. S., et al. Am J Physiol Lung Cell Mol Physiol 2008, 295 (2), L240-63). Recently, two porcine models of cystic fibrosis were developed that demonstrate all of the clinical manifestations of the human disease, including meconium ileus, pancreatic insufficiency, and lung disease. See, e.g., Rogers, C. S., et al. Science 2008, 321 (5897), 1837-41; Meyerholz, D. K., et al. Am J Respir Crit Care Med 2010, 182 (10), 1251-61; Stoltz, D. A., et al. Sci Transl Med 2010, 2 (29), 29ra31; and Meyerholz, D. K., et al. Am J Pathol 2010, 176 (3), 1377-89. In addition, similarity of porcine and human organs has led to a large effort to develop them as a source of organs for xenotransplantation (see, e.g., Cooper, D. K., et al. Annu Rev Med 2002, 53, 133-47). Finally, the reproductive characteristics of swine are favorable for their use as a model (See Table 1). Their relatively fast maturation rate and the large number of offspring generated from a single sow in one year allow a colony to rapidly expand. This is particularly important for a X-linked recessive disease like DMD.

TABLE 1

Reproductive characteristics of several species (values are approximate).

| Species | Gestation time | Sexual maturity | Offspring per delivery | Deliveries per year | Offspring per year |
|---|---|---|---|---|---|
| Mouse | 20-22 d | 40-60 d | ~6 | ~17 | 100 |
| NH primate | 150-175 d | 4-5 yr | 1 | 2 | 1-2 |
| Dog * | 63 d | 6-8 mo | 8 | 1 | 6-10 |
| Pig # | 114 d | 6-8 mo | 6-8 | ~3 | 18-24 |

* based on Golden Retriever;
based on Yucatan miniature pig

Musculoskeletal diseases, such as Duchenne muscular dystrophy, Becker muscular dystrophy, or DMD-associated dilated cardiomyopathy, have not been widely studied in pigs, primarily because the vast majority of pigs are used for commercial pork production, where the average lifespan is 6-8 months, and any pigs displaying poor health are culled from the herd. However, skeletal muscle tissue is highy conserved through evolution, and pig and human skeletal muscle very similar with only minor structural differences. Importantly, pigs are an excellent model of human cardiovascular disease and exercise physiology due to similarities in the cardiovascular system and cardiac muscle. See, e.g., Hastings, A. B., et al. J Appl Physiol 1982, 52 (4), 1077-83; Melzer, W., et al. Acta Physiol Scand 2001, 171 (3), 367-78; Dixon, J. A., et al. Circ Heart Fail 2009, 2 (3), 262-71.

The porcine genome project was recently completed. Porcine DMD shows remarkable similarity to human in gene sequence and genomic structure. The full-length porcine dystrophin protein is 94% identical to human dystrophin, and orthologous alternatively spliced isoforms have also been identified. Additionally, dystrophin protein expression in the porcine retina has been characterized and is similar to that seen in humans. See, e.g., Bordais, A., et al. Neuromuscul Disord 2005, 15 (7), 476-87.

The invention includes animals in which only one allele of a targeted gene (e.g., DMD) is disrupted, with the other allele remaining unaffected. These animals, which are referred to herein as "heterozygous" or "hemizygous" animals, can be used, for example, as models to study the development or progression of a disease (for example, Duchenne muscular dystrophy, Becker muscular dystrophy, or DMD-associated dilated cardiomyopathy) in heterozygous animals. Further, these animals can be used in breeding approaches to generate male animals carrying a disrupted or mutated allele of the targeted gene on the X chromosome.

The heterozygous animals (i.e., carrier females) of the present invention can also be used as animal models themselves, for example, in the case of diseases caused by autosomal dominant mutations, or where disruption of one allele of the targeted gene may result in some phenotypic expression of the mutation that is less severe than disruption of both alleles (or disruption of one allele in a male animal for a gene located on the X-chromosome, such as DMD). For example, the heterozygous pigs of the present invention can be used to study Duchenne muscular dystrophy, Becker muscular dystrophy or DMD-associated dilated cardiomyopathy in females with one disrupted allele that display symptoms of these diseases (i.e., manifesting carriers).

Also included in the invention are mutant DMD animals such that a mutated form of a protein (e.g., dystrophin) that retains some function is produced. For example, this technique may be used to introduce mutations in DMD that result in Becker muscular dystrophy or DMD-associated dilated cardiomyopathy in a mutant animal.

Also included in the invention are homozygous mutant animals (i.e., females), in which both alleles of a target gene (e.g., DMD) are disrupted or mutated, by the same or different mutations. In addition to being obtainable by breeding approaches involving hemizygous animals, homozygous mutant animals can also be obtained using an approach in which a cell (e.g., a fetal fibroblast) including a mutation in one allele, such as a cell obtained from an animal produced using the method summarized above, is subjected to gene targeting by homologous recombination to achieve modification of the remaining allele. The resulting donor cell can then be used as a source of a modified nucleus for nuclear transfer into a recipient cell, such as an enucleated oocyte, leading to the formation of a homozygous mutant embryo which, when implanted into a surrogate female, develops into a homozygous mutant animal.

A target gene (e.g., a DMD gene) can be subject to genetic modification in any appropriate cell type of a species for which it is desired to create an animal model of a disease associated with mutation of the gene, according to the invention. As is understood in the art, it is necessary to be able to culture and carry out homologous recombination in a cell that is to be used as a donor cell. A particular example of such a cell, which is described in more detail below in connection with pigs, in the experimental examples, is the fetal fibroblast. These cells can be obtained using, for example, the approach described in U.S. Pat. No. 7,547,816 and other references cited herein.

The invention also includes the use of other cell types that may be present in the cell preparations obtained using the method described in U.S. Pat. No. 7,547,816. Additional examples of cells that can be used as donor cells in making the transgenic animals of the invention include other fetal cells, placental cells, or adult cells. Specific examples of such cells for gene targeting include differentiated cells such as fibroblasts, epithelial cells, neural cells, epidermal cells, keratinocytes, hematopoietic cells, melanocytes, chondrocytes, B-lymphocytes, T-lymphocytes, erythrocytes, macrophages, monocytes, placental, and muscle cells.

If a cell to be genetically altered is derived from an embryo or a fetus, the cell (e.g., a fetal cell or placental cell) can be isolated at any time during the gestation period until the birth of the animal, which may or may not be itself genetically altered. In the case of a pig, such cells can be obtained, for example, between 20 to 90 days of gestation, between 25 to 60 days of gestation, between 30 to 45 days of gestation, or between 35 to 40 (e.g., at 35 days) of gestation. The time periods for obtaining cells from other animals is known in the art (see, e.g., U.S. Pat. Nos. 7,420,099 and 7,928,285).

Gene targeting carried out to make the cells and animals of the invention can result in gene inactivation by disruption, removal, modification, or replacement of target gene sequences. For example, inactivation can take place by the insertion of a heterologous sequence and/or a stop codon into a target gene. As is known in the art, inserted sequences can replace previously existing sequences in a gene or can be added to such sequences, depending on the design of the targeting construct. In another example, described in the Examples herein, deletion of a sequence using homologous recombination results in a frameshift mutation that yields a prematurely truncated and non-functional protein.

As is known in the art, the design of targeting constructs can be altered, depending upon whether it is desired to completely knock out the function of a gene or to maintain some level of reduced function. In the case of DMD, for example, complete knock out of function would be consistent with the most severe forms of DMD in which there is no dystrophin present. However, other less dramatic changes may be desirable for the generation of models of disease maintaining some DMD function. These would include mutations in which some DMD function is retained, such as in the production of a mutation that leads to an abnormal version of dystrophin that retains some function, as in Becker muscular dystrophy. Such changes may be achieved by, for example, replacement with sequences that are identical to wild-type sequences, except for the presence of specific mutations giving rise to features of the target disease. In other approaches, coding sequences are not altered or are minimally altered and, rather, sequences impacting expression of a target gene, such as promoter sequences, are targeted. In any case, selectable marker insertion is often desirable to facilitate identification of cells in which targeting has occurred. If desired, such markers or other inserted sequences can later be removed by, e.g., cre-lox or similar systems.

A "humanized" DMD model (i.e., a DMD− animal expressing a mutant human DMD transgene) can be made numerous ways, including, but not limited to: i) introducing a mutant human DMD cDNA, partial mutant human DMD gene, or entire human DMD gene carrying a mutation into animal (e.g., porcine) DMD− cells, selecting for mutant human DMD gene insertion, and using these cells as nuclear donors in somatic cell nuclear transfer, and ii) introducing a mutant human DMD cDNA, partial mutant human DMD gene, or entire human DMD gene carrying a mutation to animal DMD− cells into matured oocytes, fertilizing, then transferring to a recipient female.

As is known in the art, targeted gene modification requires the use of nucleic acid molecule constructs having regions of homology with a targeted gene (or flanking regions), such that integration of the construct into the genome alters expression of the gene, either by changing the sequence of the gene and/or the levels of expression of the gene. Thus, to alter a gene, a targeting construct is generally designed to contain three main regions: (i) a first region that is homologous to the locus to be targeted (e.g., the DMD gene or a flanking sequence), (ii) a second region that is a heterologous polynucleotide sequence (e.g., encoding a selectable marker, such as an antibiotic resistance protein) that is to specifically replace a portion of the targeted locus or is inserted into the targeted locus, and (iii) a third region that, like the first region, is homologous to the targeted locus, but typically is not contiguous with the first region of the genome. Homologous recombination between the targeting construct and the targeted wild-type locus results in deletion of any locus sequences between the two regions of homology represented in the targeting vector and replacement of that sequence with, or insertion into that sequence of, a heterologous sequence that, for example, encodes a selectable marker. Use of such promoters may not be required in cases in which transcriptionally active genes are targeted, if the design of the construct results in the marker being transcribed as directed by an endogenous promoter. Exemplary constructs and vectors for carrying out such targeted modification are described herein. However, other vectors that can be used in such approaches are known in the art and can readily be adapted for use in the invention.

In order to facilitate homologous recombination, the first and third regions of the targeting vectors (see above) include sequences that exhibit substantial identity to the genes to be targeted (or flanking regions). By "substantially identical" is meant having a sequence that is at least 80%, preferably at least 85%, preferably at least 90%, more preferably at least 95%, even more preferably at least 98%, and even more preferably 100% identical to that of another sequence. Sequence identity is typically measured using BLAST® (Basic Local Alignment Search Tool) or BLAST® 2 with the default parameters specified therein (see, Altschul et al., J. Mol. Biol. 215: 403-410, 1990; Tatiana et al., FEMS Microbiol. Lett. 174: 247-250, 1999). These software programs match similar sequences by assigning degrees of homology to various substitutions, deletions, and other modifications. Thus, sequences having at least 80%, preferably at least 85%, preferably at least 90%, more preferably at least 95%, even more preferably at least 98%, and even more preferably 100% sequence identity with the targeted gene loci can be used in the invention to facilitate homologous recombination.

The total size of the two regions of homology (i.e., the first and third regions noted above) can be, for example, approximately between 2-25 kilobases (for example, approximately between 4-20 kilobases, approximately between 5-15 kilobases, or approximately between 6-10 kilobases), and the size of the second region that replaces a portion of the targeted locus can be, for example, approximately between 0.5-5 kilobases (for example, approximately between 1-4 kilobases or approximately between 3-4 kilobases).

The targeting constructs can be included within any appropriate vectors, such as plasmid or viral vectors (e.g., adenovirus or adeno-associated virus (AAV) vectors), which can be introduced into cells using standard methods including, for example, viral transduction, electroporation, or microinjection. One preferred example of the invention, which is described in detail in the experimental examples, below, employs a recombinant adeno-associated viral vector (rAAV), which can be made by standard methods or produced commercially.

Recombinant adeno-associated virus has been used to deliver gene targeting vectors to cell lines and primary cells (see, e.g., Russell, D. W., et al. Nat Genet 1998, 18 (4), 325-30). For example, rAAV has been used to introduce two different targeted modifications to the porcine CFTR gene. See, e.g., Rogers, C. S., et al. J Clin Invest 2008, 118 (4), 1571-7, U.S. Pat. No. 7,989,675 and U.S. patent application Ser. No. 12/283,980.

The use of an rAAV to deliver the targeting construct offers many benefits. First, rAAV1 (and other rAAV serotypes) infects pig fetal fibroblasts with nearly 100% efficiency. See, e.g., Rogers, C. S., et al. J Clin Invest 2008, 118 (4), 1571-7. Second, rAAV infection of pig fetal fibroblasts results in little or no cell toxicity. Third, rAAV infection results in the delivery of a single-stranded gene-targeting construct directly to the nucleus, the amount of DNA per cell is small, and it can infect many cell types. Importantly, the ratio of homologous recombination events to random integrations is more favorable than that seen with electroporation of lipid-mediated transfection. See, e.g., Vasquez, K. M., et al. Proc Natl Acad Sci USA 2001, 98 (15), 8403-10.

The methods of the invention, employing rAAV vectors, resulted in high levels of gene targeting efficiency in these somatic cells, as compared to prior methods. Central to the methods of the invention is the fact that the entire procedure was performed in a time-sensitive manner, because excessive cell culture time (for example, more than 30 days) negatively impacts nuclear transfer efficiency (Lai et al., Cloning and Stem Cells 5(4):233-241, 2003). Following fibroblast harvest from day 35 fetuses, the cells were frozen within 48 hours. The use of an AAV vector to deliver the gene targeting construct allowed targeting to begin 24 hours after thawing cells and required no cell detachment and re-attachment, which is required in other methods. Multiple cell detachment and re-attachment events (trypsinization) are thought to decrease the ability of a cell to serve as a nuclear donor in nuclear transfer. Further, G418 selection in 48 96-well plates prevents the need for the more conventional, time-consuming isolation of resistant clones with cloning rings. The screen for gene targeted clones was designed such that all positive clones could be identified and frozen within a 3-5 day period. All clones were frozen by day 18, therefore the cells have been in culture approximately 20 days since being harvested from the fetus. In this aspect of the invention, reduction of the time in culture increases the likelihood that cells used as nuclear donors are viable, normal, and euploid.

Accordingly, the invention provides a method of gene-targeting cells, such as pig cells (e.g. pig fetal fibroblasts), in which the number of days in culture (during which targeting and selection takes place) is preferably less than 30 days, preferably 25-29 days, preferably 20-24 days, and more preferably 19, 18, 17, 16, 15, or fewer days. To facilitate this method, the selection can take place in multi-well plates, as described further below. Further, the cells may be frozen shortly after harvest (for example, within 24, 48 or 96 hours). After cell thawing (or after harvest, if the cells are not previously frozen), gene targeting with an rAAV vector can be carried out within, for example, 12, 24, 36 or 48 hours, without the use of multiple detachment/re-attachment events, and selection can proceed in an expedited manner, such as by use of multi-well plates (e.g., 96 well plates), prior to freezing.

Other types of vectors, or more specifically other types of targeting construct delivery methods, are also available to those of skill in the art and may be used in the present invention. Such methods include cell transfection methods, including calcium phosphate, lipofection, electroporation, and nuclear injection, all of which can be used to deliver the targeting construct. If the gene is transcriptionally active in the cell being used, then a promoterless selectable strategy can be employed, so that antibiotic resistance will only be found in cells that have had a recombination event within the transcribed unit.

Genetically targeted cells are typically identified using a selectable marker, such as neomycin. If a cell already contains a selectable marker, however, a new targeting construct containing a different selectable marker can be used. Alternatively, if the same selectable marker is employed, cells can be selected in the second targeting round by raising the drug concentration (for example, by doubling the drug concentration), as is known in the art. As is noted above, targeting constructs can include selectable markers flanked by sites facilitating excision of the marker sequences. In one example, constructs can include loxP sites to facilitate the efficient deletion of the marker using the cre/lox system. Use of such systems is well known in the art, and a specific example of use of this system is provided below, in the experimental examples.

Upon obtaining cells in which a target gene (e.g., a DMD gene) has been targeted (one or both alleles, as described above), nuclear transfer can be carried out. Optionally, the genetically modified nuclear donor cells can be frozen prior to nuclear transfer. Recipient cells that can be used in the invention are typically oocytes, fertilized zygotes, or two-cell embryos, all of which may or may not have been enucleated. Typically, the donor and the recipient cells are derived from the same species. However, it is possible to obtain development from embryos reconstructed using donor and recipient cells from different species.

Recipient oocytes can be obtained using methods that are known in the art or can be purchased from commercial sources. As is known in the art, the donor nucleus or the donor cell itself can be injected into the recipient cell or injected into the perivitelline space, adjacent to the oocyte membrane. The nuclear transfer complex formed in this manner can be activated by standard methods, which may involve electrical fusion/activation or electrical fusion/chemical activation, as is described further below. Further processing of the nuclear transfer complex, including implementation of the complexes into surrogate mothers, is described further below.

The transgenic animals of the invention can be used in the identification and characterization of drug and other treatment methods for the disease or condition associated with mutation of the gene targeted according to the invention. In these methods, for example, a candidate therapeutic agent can be administered to an animal and the impact of the agent on a feature of the disease exhibited by the animal can be monitored. Optionally, the methods can also involve exposure of the animals to environmental or other conditions known to contribute to or exacerbate the disease or condition. For example, in the case of Duchenne muscular dystrophy, Becker muscular dystrophy, or DMD-associated dilated cardiomyopathy, animal models having impaired function in the DMD gene can be used to monitor the effect of a therapeutic agent, such as a drug, on dystrophin function or production. In another example, gene- and cell-based therapies for Duchenne muscular dystrophy, Becker muscular dystrophy, and DMD-associated dilated cardiomyopathy can be administered in such an animal and the animal may be monitored for the effects on production and function of dystrophin, and further can be used to assess the effect and the impact on progression (or reversal) of Duchenne muscular dystrophy, Becker muscular dystrophy, or DMD-associated dilated cardiomyopathy.

With the porcine model of the invention, it is possible to test hypotheses that lead to new treatments, diagnostics, imaging technologies and medical devices, and to evaluate potential therapies for Duchenne muscular dystrophy, Becker muscular dystrophy, and DMD-associated dilated cardiomyopathy. Likely activities involving the present invention may include evaluating current and future therapeutics for toxicity, pharmacokinetics and efficacy within the same animal. Medical devices makers may study the efficacy of stents (and other medical devices and products) in a relevant, diseased setting. And in the context of medical instruments, noninvasive ultrasound imaging may be evaluated to diagnose and chart the progression of Duchenne muscular dystrophy, Becker muscular dystrophy, or DMD-associated dilated cardiomyopathy.

Availability of animal models for Duchenne muscular dystrophy, Becker muscular dystrophy, and DMD-associated dilated cardiomyopathy allows new investigations and tests of therapeutics in the heart, skeletal muscles and other organs and affected primarily or secondarily by Duchenne muscular dystrophy, Becker muscular dystrophy, and DMD-associated dilated cardiomyopathy. The screening methods of the invention can be carried out to test the efficacy of new compounds, combinations of new and old compounds, diagnostics, non-pharmaceutical treatments (such as gene- and cell-based therapies), medical devices, and combinations of the foregoing.

The following Examples are meant to illustrate the invention and are not meant to limit the scope of the invention in any way.

EXPERIMENTAL EXAMPLES

Example 1

Yucatan Miniature Pigs and Cells for Gene Targeting

The Yucatan miniature pig was selected for development of a DMD model. While it possesses the same biological characteristics as domestic pigs, the Yucatan miniature pig is significantly smaller. Most domestic pig breeds reach 100 kg in less than six months and can achieve weights of 250-300 kg within a few years. Yucatan miniature pigs reach a full-grown size of 65-90 kg at two years of life, which is more similar to an adult human. Therefore, the Yucatan miniature pigs are less expensive to house and feed. Additionally, this breed is more docile in nature and better suited for interactions with researchers. See, e.g., Panepinto, L. M., et al., Lab Anim Sci 1986, 36 (4), 344-7.

Due to the lack of suitable porcine embryonic stem cell lines, the standard methods for producing gene-targeted mice are not applicable in pigs (Piedrahita, J. A., Theriogenology 2000, 53 (1), 105-16). Instead, gene targeting must be achieved in a somatic cell that is then used as a nuclear donor for SCNT. While numerous cell types can be used as nuclear donors, fetal fibroblasts have been the predominate cell type for creating gene-targeted pigs. Fibroblasts previously obtained from male and female Yucatan miniature pig fetuses at day 35 of gestation were selected. Fibroblasts from the Yucatan breed behave similar to domestic pig fibroblasts in culture, gene transfer, and for SCNT (Estrada, J. L., et al. Cloning Stem Cells 2008, 10 (2), 287-96).

Example 2

Creation of a DMD Targeting Construct

As mentioned above, porcine DMD has been sequenced and annotated, and the genomic structure is similar to the human gene. Homologous recombination was used to delete exon 52 (ex52del) from porcine DMD ($DMD^{ex52del}$). Exon 52 is one of several "hotspot" exons (exons 45-55) that are commonly deleted in DMD patients (see, e.g., Hoffman, E. P., et al. Science 1987, 238 (4825), 347-50; Yokota, T., et al. Ann Neurol 2009, 65 (6), 667-76. This particular deletion provides a widely applicable DMD model that will allow studies focused on both disease pathogenesis related to dystrophin-deficiency and the development of new therapeutic interventions designed to restore function to diseased muscle.

The deletion of exon 52 results in a frameshift mutation that yields a prematurely truncated and non-functional protein. This may also induce the nonsense-mediated mRNA decay processes. In either event, no functional dystrophin protein is expected to be produced.

The DMD$^{ex52del}$ pig was selected because it has wide-ranging drug development utility, from testing late-stage small molecule pharmaceuticals to investigating new gene- and cell-based therapeutic approaches. The lack of dystrophin is ideal for testing gene replacement/augmentation strategies as well as myoblast transplant and new myogenic stem cell therapies (see, e.g., Trollet, C., et al. Expert Opin Biol Ther 2009, 9 (7), 849-66; Farini, A., et al. J Cell Physiol 2009, 221 (3), 526-34; Guglieri, M., et al. Curr Opin Pharmacol 2010, 10 (3), 331-7; Wang, Z., et al. ILAR J 2009, 50 (2), 187-98). Additionally, this model is ideal for testing exon-skipping, which involves the use of antisense oligonucleotides to facilitate the skipping of exons whose presence disrupts the open reading frame (see, e.g., Yokota, T., et al. Ann Neurol 2009, 65 (6), 667-76; Yokota, T., et al. Expert Opin Biol Ther 2007, 7 (6), 831-42). The goal for exon-skipping is for the resulting protein to retain partial function so as to generate a phenotype resembling the much less severe Becker muscular dystrophy. Exon-skipping oligonucleotides targeted to the exon 45-55 hotspot region would be predicted to give rise to a highly functional protein with the potential to encompass more than 60% of human DMD-causing mutations.

Exon 52 was deleted from porcine DMD in a two-step process. First, homologous recombination was utilized to replace exon 52 with a neomycin resistance cassette (Neo$^R$) flanked by loxP sites (FIG. 2) (SEQ ID NO: 1). While this alone leads to a dystrophin-deficient phenotype, the presence of the Neo$^R$ may negatively impact DMD mRNA expression, and could interfere with future therapeutic strategies. Therefore, the Neo$^R$ cassette was removed in a second step. Because of the current lack of Cre recombinase-expressing pigs, the Neo$^R$ cassette was removed from the DMD$^{ex52del}$ pigs after the generation of the first animals, at the cell stage. In a future step, ear-derived fibroblasts will be obtained from DMD$^{ex52del}$ pigs, infected with rAAV-Cre to excise the Neo$^R$ cassette, and then used as nuclear donors in another round of SCNT. Due to the high efficiencies of rAAV (~100%, see below) and Cre-mediated excision (>80%), Neo$^R$-excised cells will be easily obtained via a limiting dilution procedure in a series of 96-well plates.

Example 3

Using Recombinant AAV Vectors to Target the Porcine DMD Gene

Figure 2:
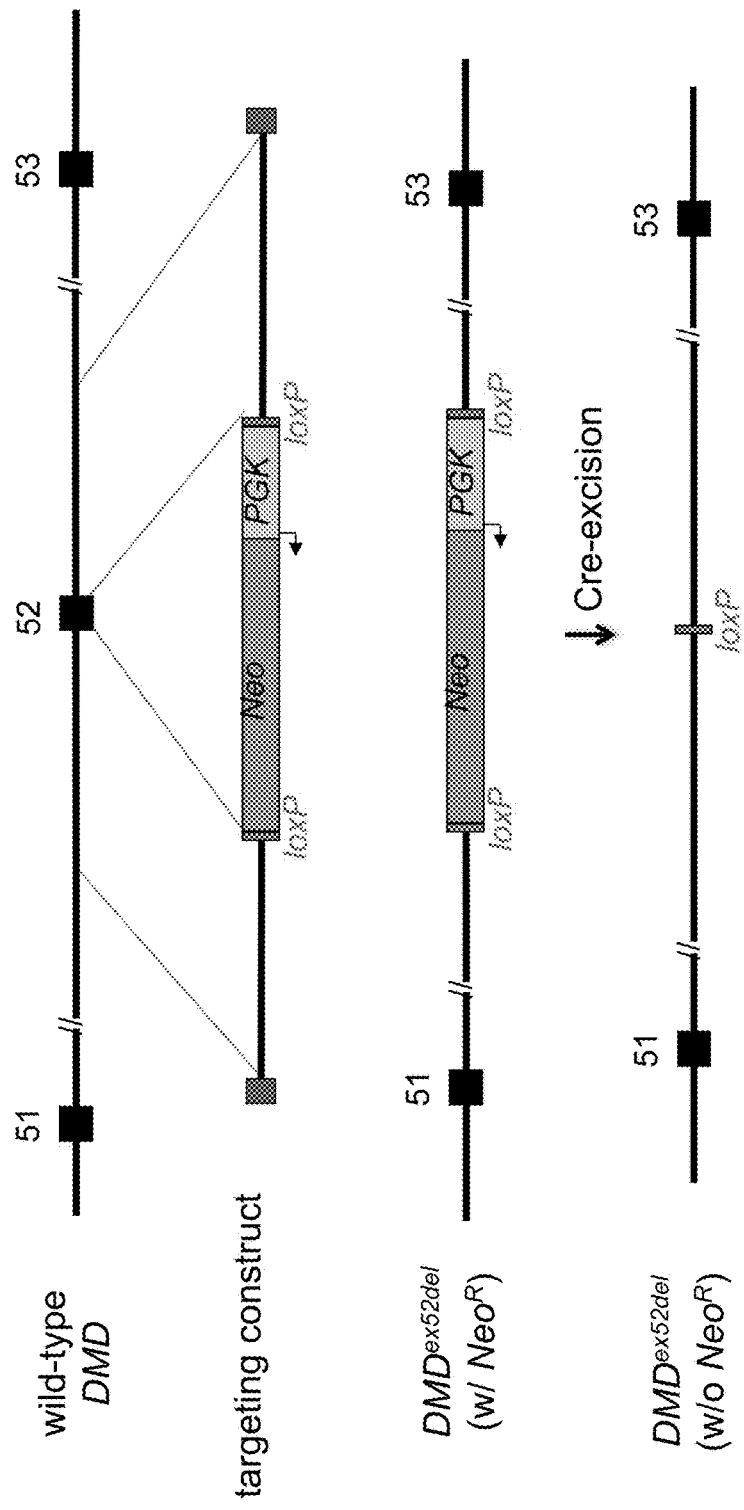
FIG. 2 shows a schematic drawing (not drawn to scale) of the gene targeting vector (SEQ. ID. NO: 1) used to delete exon 52 from porcine DMD. The initial targeted locus contains a $Neo^R$ cassette in place of exon 52. Exon 52 is Cre-excised in a subsequent step. Exons 51-53 of porcine DMD are depicted in black boxes. $Neo^R$ contains a neomycin resistance cDNA (shown in orange) driven by the phosphoglycerate kinase (PGK) promoter and flanked by loxP sites (shown in blue). The rAAV inverted terminal repeats (ITRs) are also shown in red. Each homology arm is about 1.4 kb in length.

Because of rAAV genome size constraints, the total length of the targeting vectors was limited to about 4.5 kb. The 1.7 kb Neo$^R$ was centrally located in the targeting vector, with each homology arm being ~1.4 kb (FIG. 2).

A plasmid carrying the DMD$^{ex52del}$ targeting vector was generated using standard molecular biology techniques. Proper sequence was confirmed by DNA sequence analysis. The plasmid was then submitted to the University of Iowa Gene Transfer Vector Core for production of recombinant adeno-associated virus (rAAV). rAAV was chosen because it has been used to efficiently deliver gene targeting vectors to cell lines and primary cells (Meyerholz, D. K., et al., Am J Respir Crit Care Med 2010, 182 (10), 1251-61). Additionally, rAAV has previously been used to engineer specific mutations in porcine CFTR and LDLR. See, e.g., Rogers, C. S., et al., J Clin Invest 2008, 118 (4), 1571-7; Rogers, C. S., et al., Science 2008, 321 (5897), 1837-41, U.S. Pat. No. 7,989,675; U.S. patent application Ser. Nos. 13/288,720, 13/368,312 and 13/624,967.

Example 4

Targeting DMD in Porcine Fetal Fibroblasts

Fetal fibroblasts from males were used to generate the initial DMD$^{ex52del}$ pigs. DMD$^{ex52del}$ female cells were also generated and serve as the basis for a breeding herd. Approximately 1.5×10$^6$ Yucatan miniature pig fetal fibroblasts—both male and female—were infected with rAAV1 (MOI≅100,000) carrying the DMD$^{ex52del}$ targeting vector. After 24 hours, cells were transferred to a series of 96-well plates and G418 (100 µg/ml) was added to the media for selection of targeted cells. Fourteen days later, surviving cells were observed in 20-40% of wells, and each well of the 96-well plates were "replicated" by splitting among three plates: 1) 96-well culture plates for cell expansion, 2) 96-well culture plates for potential cryopreservation, and 3) 96-well PCR plates for cell lysis.

Cell lysates were screened by PCR to identify wells containing gene-targeted clones and any PCR-positive clones were frozen. The PCR screen exploited the size difference caused by replacing the 118 by exon 52 with the ~1.7 kb Neo$^R$ (See FIGS. 3A and 3B). PCR identified 30 DMD$^{ex52del}$ male cell lines and 21 DMD$^{ex52del/+}$ female cell lines.

By the time DMD$^{ex52del}$ cells were frozen, they had been in culture only 15-17 days. This short time frame is important as the longer cells are in culture, the less efficient they are as nuclear donors. Positive clones from the "cell expansion" plates were also passaged to provide genomic DNA for downstream applications. Because G418-selected fetal fibroblasts often senesce before large quantities of genomic DNA can be obtained, we isolated genomic DNA from the 96-well expansion plate and used whole-genome amplification (REPLI-g, Qiagen) to provide DNA for Southern blot analysis.

Figure 3:
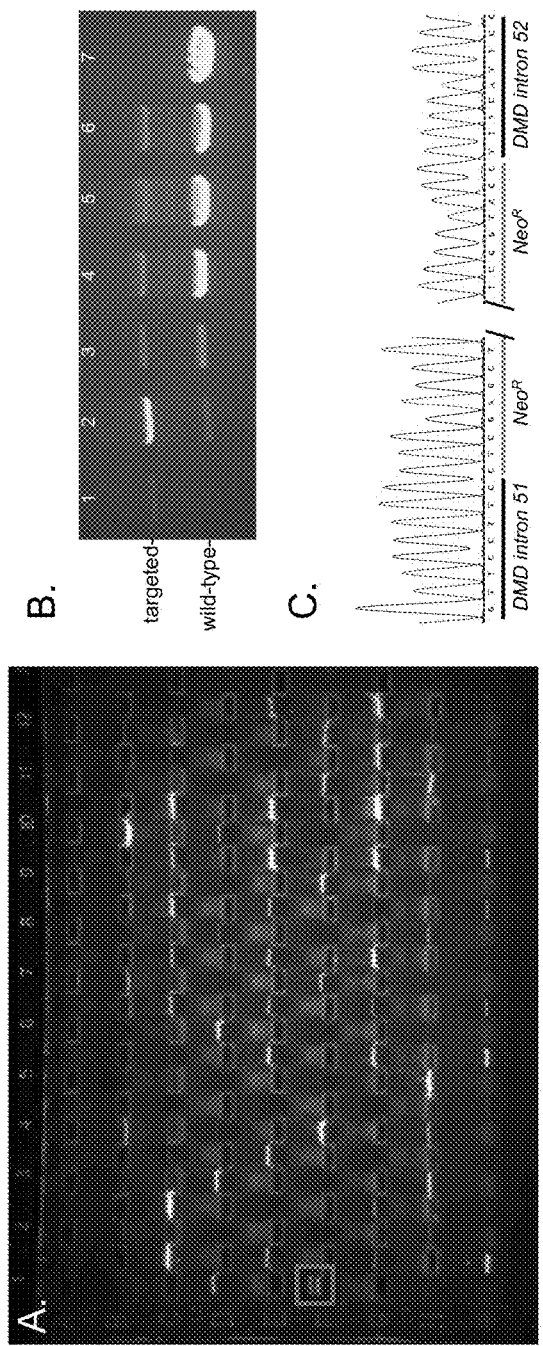
FIG. 3 shows PCR screen identified $DMD^{ex52del}$ cells.

DNA sequence analysis was used to confirm the proper targeting site (FIG. 3C). Furthermore, Southern blots with DMD- and Neo$^R$-specific probes were used to identify clones with a targeted DMD allele and that were free of random integration. Eleven DMD$^{ex52del}$ male cell lines and seven DMD$^{ex52del/+}$ female cell lines were identified to date that meet the above criteria—processing all of the PCR-positive cell lines was not necessary; however, those cells and DNA have been preserved, if needed. It is believed the quality and quantity of these cells are ideal for nuclear transfer, and they will be used to generate DMD-targeted pigs.

Example 5

Nuclear Transfer and Propagation

DMD$^{ex52del}$ male and female cells were used for somatic cell nuclear transfer (SCNT) to produce live male and female DMD$^{ex52de;}$ offspring. As alluded to in Example 2, ear-derived fibroblasts were obtained from the first male and female piglets, and Neo$^R$ was excised, thus producing DMD$^{ex52del}$ fibroblasts suitable for future rounds of SCNT. The SCNT process is described, for example, in U.S. Pat. No. 7,989,675, and in U.S. patent application Ser. Nos. 13/368,312 and 13/624,967.

Figure 4:
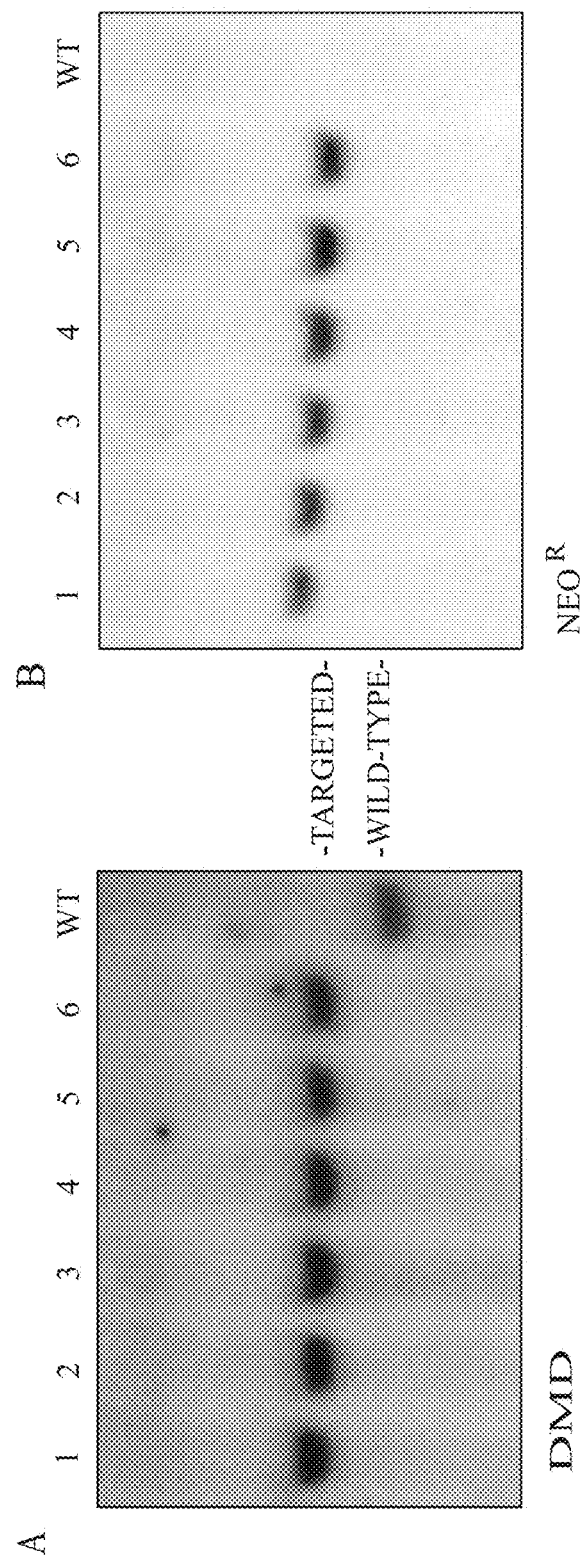
FIG. 4 shows a genomic Southern blot from DMD$^{ex52del}$ male pig fetuses.

As mentioned previously, primary fibroblasts often senesce after extended time in culture, especially during antibiotic selection. Therefore, obtaining adequate numbers of gene-targeted cells for SCNT can be a challenge. We sought to generate a nearly unlimited supply of DMD$^{ex52del}$ fibroblasts by employing a process called "rejuvenation". This was accomplished with SCNT using male DMD$^{ex52del}$ fibroblasts (generated as described above) and harvesting day 35 fetuses. Fetal fibroblasts were then isolated using standard methods. Fifteen DMD$^{ex52del}$ fetuses were obtained, yielding ~400 million cells. PCR and genomic Southern blots confirmed the DMD allele to be properly targeted (FIG. 4), and was verified by DNA sequence analysis. Because these cells were cultured for only 2 days before freezing, they should be more suitable for SCNT, as well as other procedures such as Neo$^R$ cassette excision. Importantly, this also demonstrates that DMD$^{ex52del}$ SCNT embryos can produce a pregnancy, which is an excellent predictor of success. In our experience, more than 85% of day 35 pregnancies proceed to full term.

Initial DMD-targeted males and carrier females generated via SCNT will also be used for herd propsgation. Wild-type males can be bred with carrier females to yield 25% affected males, 25% wild-type males, 25% carrier females, and 25% wild-type females. Problems are not anticipated with this breeding strategy (based on human and canine data) or with intergenerational phenotype stability (based on experience with cystic fibrosis pigs). However, if either should become a problem, all DMD$^{ex52del}$ pigs and controls can be propagated via SCNT.

Example 6

Characterization and Phenotype

Figure 5:
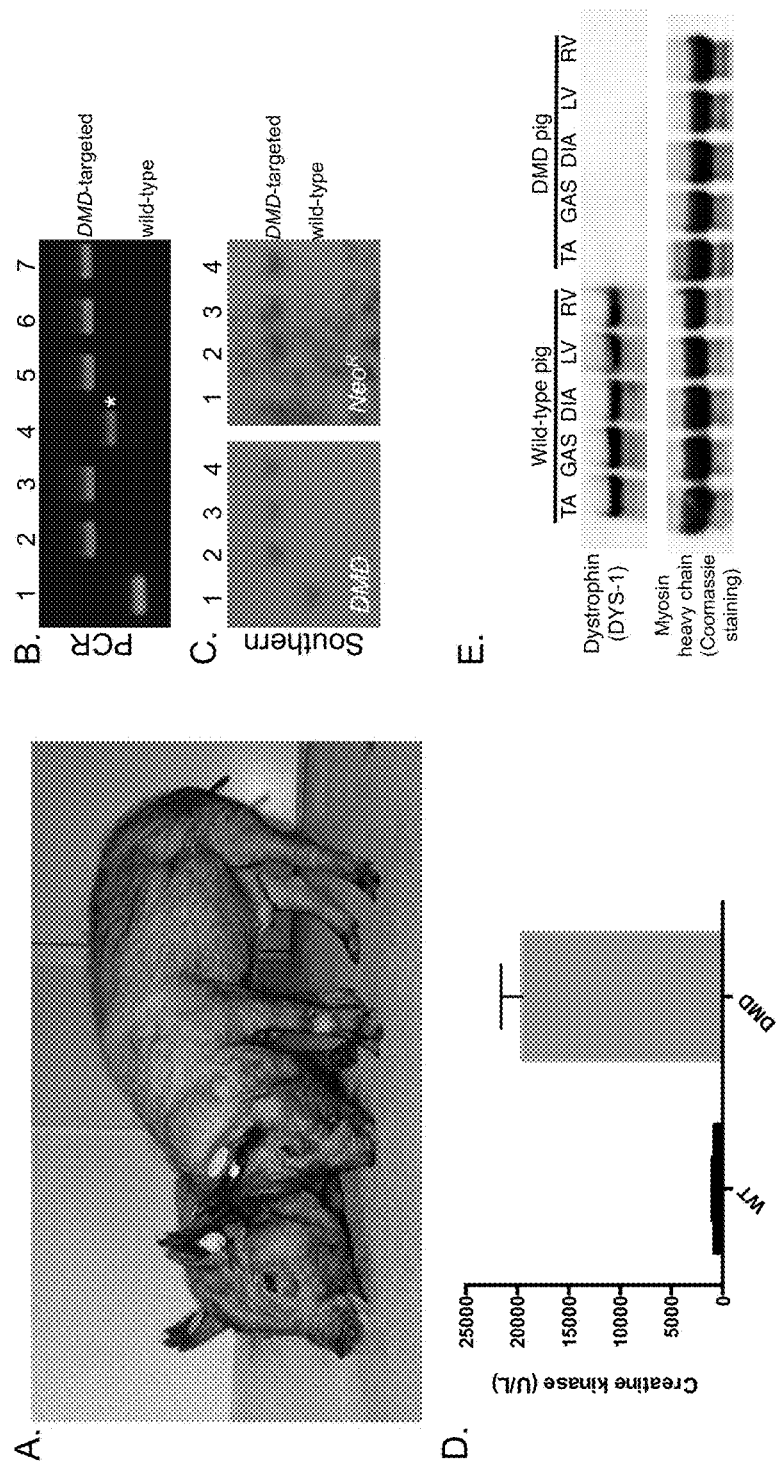
FIG. 5 shows initial characterization of DMD pigs.
Figure 6:
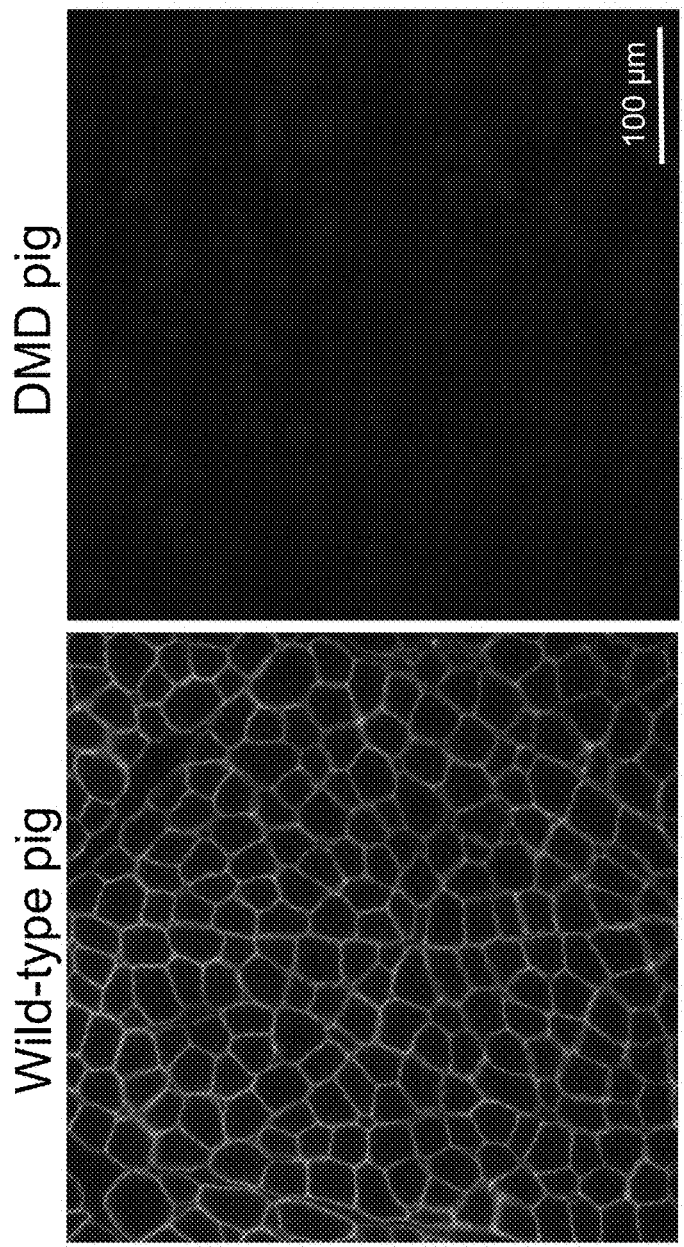
FIG. 6 shows immunohistochemical detection of dystrophin. Rabbit polyclonal anti-dystrophin (C-terminal) antibody was used to detect dystrophin in skeletal muscle (tibialis anterior). The left frame shows staining in a Wild-type pig, the right frame shows a lack of staining in a DMD pig.
Figure 7:
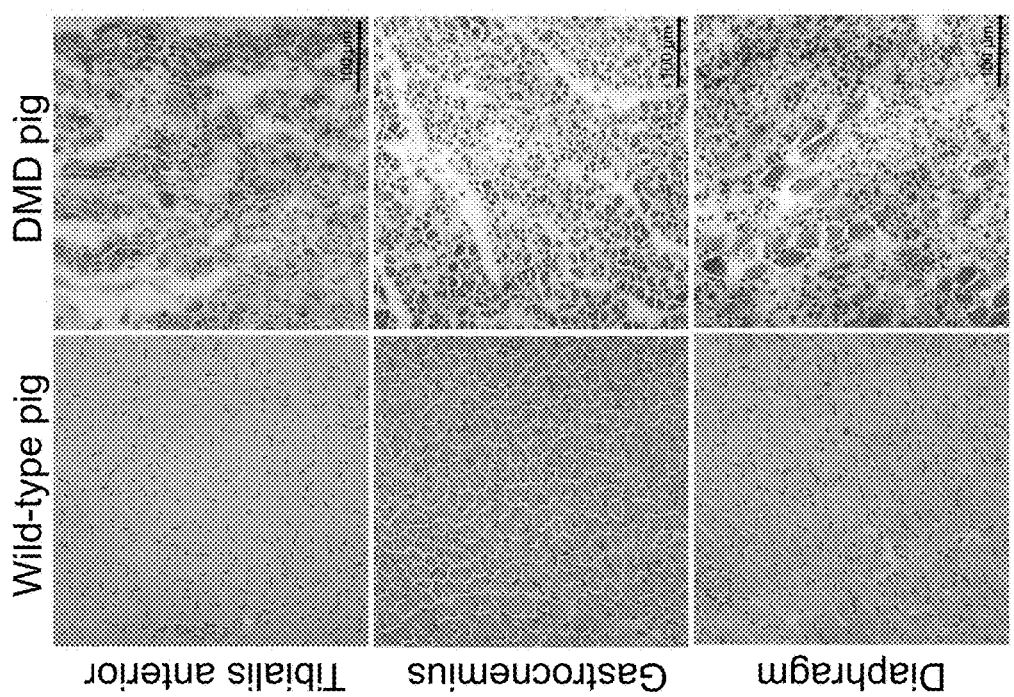
FIG. 7 shows hematoxylin and eosin staining of muscle from a wild-type pig (left hand column) and a DMD pig (right hand column). The DMD pig shows classic muscle degeneration and regeneration.

The first DMD pigs were produced using the methods described herein and initial characterization confirms a dystrophic phenotype. The initial assessment of the DMD pigs is presented in FIG. 5. To summarize, FIG. 5A depicts two DMD pigs at fifteen weeks of age. Proper DMD targeting was confirmed via PCR, Southern blot (FIGS. 5B and 5C), and DNA sequencing (data not shown). Creatine kinase levels from DMD pigs are dramatically elevated relative to age-matched wild-type controls (FIG. 5D). Western blot analysis confirmed that no full-length dystrophin is produced in these pigs (FIG. 5E). Muscle from a DMD pig euthanized at four days of age was processed for immunohistochemistry and histology. Immunohistochemical staining of tibialis anterior shows the complete absence of dystrophin in the DMD pig (FIG. 6). H&E staining of tibialis anterior, gastrocnemius, and diaphragm depict typical dystrophic features of degeneration and regeneration (FIG. 7). Additional skeletal muscle samples were similar. We have observed that DMD pigs have enlarged tongues, possibly the pseudohypertrophy that is seen in humans and other animal models. This is partially seen in the pig on left in FIG. 5A. They also exhibit a slight pelvic tilt similar to what has been seen in golden retriever model. Finally, we are beginning to observe that DMD pigs are less stable when walking on inclines and declines, whereas wild-type controls have no trouble.

Gene targeting efficiency and SCNT activity is summarized in Table 2.

TABLE 2

Summary of DMD targeting efficiency and SCNT activity

| | Gene targeting efficiency* | Number of transfers | Embryos per transfer (average) | Pregnancy rate† | Live pigs per litter |
|---|---|---|---|---|---|
| Male | 1.4% | 3 | 150 | 100% | 9 |
| Female | 0.9% | 3 | 137 | 34% | 8 |

*Gene targeting efficiency reported as percentage of G418$^R$ clones that were properly targeted, as determined by PCR.
†Pregnancy rate refers to full-term gestation.

Other Embodiments

Unless otherwise defined herein, all technical and scientific terms used herein have the ordinary meaning as commonly understood by one of ordinary skill in the art to which this invention pertains. Although methods and materials similar or equivalent to those described herein can be used in the practice or testing of the present invention, suitable methods and materials are described herein.

Although the invention has been described above in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

Following long-standing patent law convention, the terms "a," "an," and "the" refer to "one or more" when used in this application, including the claims. Thus, for example, reference to "a subject" includes a plurality of subjects, unless the context clearly is to the contrary (e.g., a plurality of subjects), and so forth.

The contents of the articles, patents, and patent applications, and all other documents and electronically available information mentioned or cited herein, are hereby incorporated by reference in their entirety to the same extent as if each individual publication was specifically and individually indicated to be incorporated by reference. Applicants reserve the right to physically incorporate into this application any and all materials and information from any such articles, patents, patent applications, or other documents.

Other embodiments are within the following claims.

What is claimed is:

1. A transgenic swine comprising a targeted mutation of an endogenous dystrophin gene (DMD) in all of its cells,
    wherein the transgenic swine
        lacks expression of any dystrophin,
        has an enlarged tongue, and
        has elevated creatine kinase levels relative to age-matched wild-type controls,
    wherein said mutation comprises a deletion or a disruption of exon 52 in said endogenous DMD, and
    wherein the swine lacks a heterologous selectable marker.

2. The transgenic swine of claim 1, wherein the swine is a Yucatan miniature pig.

3. An isolated cell of the transgenic swine of claim 1.

4. The transgenic swine of claim 1, further comprising a loxP site to facilitate the efficient deletion of the heterologous selectable marker.

5. The transgenic swine of claim 1, which is a male.

6. The transgenic swine of claim 1, which is a female.

7. The transgenic swine of claim 1 wherein the cells of said swine are free of a random integration event.

* * * * *

SEQUENCE LISTING

<160> NUMBER OF SEQ ID NOS: 3

<210> SEQ ID NO 1
<211> LENGTH: 4501
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 1

```
tactgcaggg gaagtaagaa aatgtaatac tgatatacag gagagaaggg aagtggaggg      60
aagggaggag acccagggag atccaagaaa atctgatagc aaaggtgacc tgggactcat     120
ttctgaggaa aacctctaag ggaaacagga cagagagcag tttcccctaa ccttctgtct     180
agccctcttc ctggcaccat gtacagttac tctgaatcac tctgtgtaaa gaagaaaaaa     240
gcatgtgcat tatctaggca gatgggcctt aaacagcctc tcaaagttcc cacctgatga     300
tctctgatat tgcaatgatc tctgatatta cacaaggagg gcatccaaag agcagagaga     360
tgtctagatc tgaaagtacc actgcataca ggagagaaat atggtccagg aagcaacggc     420
ctccttacac caacaactga ggatatgagg gagagagcgg cgtctccatg gatgccagcc     480
tagacacatg acaaatgagg atcaaatgtt ctgccacacc tatgttcacc atatccacca     540
tttcatgctt tgcaactata taagcttgga ttgatgaaaa ttatattttc tctattgcat     600
ggaattacat gcagttactg aaaaaataac gatatggact gaaaaactta gttacaatag     660
ttatacaata ttttttttgg tcttttttgcc tttttaggg ccgctcccgt ggcatatgga     720
ggttctcagg ctaggtgtcc aatcggagct gtagccacca gctatgcca gagccacagc     780
aacgccagat ccgagccaca tctgcgacct acaccacaac tcacagcaac accggaatca     840
taacccactt agcgaggcca gggatcgaac atgtaacctc atggttccta gtcggattcg     900
ttaaccactg tgccacgacg ggaactccag ttatacaatt ctttagcact attttttgt      960
cttttaggt ccacacctgt ggcatatgga agttcccagg ctaggggttg aatgggagct     1020
gtaactgcca gcccacatca cagtcacagc aacatggat ccgaaccacc tctgcaacct     1080
acaccacagc atgctgcaat gctggatctt taacccactg agaggggcca ggaatcagat     1140
ccgcatgcat ccttatggat atcagtaggg ttcgttatag ctgaggcaag ataggaactc     1200
tgtctttagc actatttta taaattttgt ggaggcatat gaacttaagt tatcctagaa     1260
aattttcata cgtcttttct taagtttcac atgcctgtta aaaaagaga cttattttgg     1320
gagttccctg gtagcttagt ggttaatgat ttgtcattgc cattgctatg gttcaggttt     1380
tatccctggc atggggaatg taaggtaccg agctcggatc cactagtaac ggccgccagt     1440
gtgctggaat tcggcttcaa caacttcgta taatgtatgc tatacgaagt tatcagtact     1500
tttcccaagg cagtctggag catgcgcttt agcagccccg ctgggcactt ggcgctacac     1560
aagtggcctc tggcctcgca cacattccac atccaccggt aggcgccaac cggctccgtt     1620
ctttggtggc cccttcgcgc caccttctac tcctccccta gtcaggaagt tccccccgc      1680
cccgcagctc gcgtcgtgca ggacgtgaca aatggaagta gcacgtctca ctagtctcgt     1740
gcagatggac agcaccgctg agcaatggaa gcgggtaggc ctttgggca gcggccaata     1800
gcagctttgc tccttcgctt tctgggctca gaggctggga aggggtgggt ccggggcgg      1860
gctcagggc gggctcaggg gcggggcggg cgcccgaagg tcctccggag gcccggcatt     1920
ctgcacgctt caaaagcgca cgtctgccgc gctgttctcc tcttcctcat ctccgggcct     1980
ttcgacctgc agccaatatg ggatcggcca ttgaacaaga tggattgcac gcaggttctc     2040
cggccgcttg ggtggagagg ctattcggct atgactgggc acaacagaca atcggctgct     2100
ctgatgccgc cgtgttccgg ctgtcagcgc aggggcgccc ggttcttttt gtcaagaccg     2160
acctgtccgg tgccctgaat gaactgcagg acgaggcagc gcggctatcg tggctggcca     2220
cgacgggcgt tccttgcgca gctgtgctcg acgttgtcac tgaagcggga agggactggc     2280
```

```
tgctattggg cgaagtgccg gggcaggatc tcctgtcatc tcaccttgct cctgccgaga    2340
aagtatccat catggctgat gcaatgcggc ggctgcatac gcttgatccg gctacctgcc    2400
cattcgacca ccaagcgaaa catcgcatcg agcgagcacg tactcggatg gaagccggtc    2460
ttgtcgatca ggatgatctg gacgaagagc atcagggggct cgcgccagcc gaactgttcg    2520
ccaggctcaa ggcgcgcatg cccgacggcg aggatctcgt cgtgacccat ggcgatgcct    2580
gcttgccgaa tatcatggtg gaaaatggcc gcttttctgg attcatcgac tgtggccggc    2640
tgggtgtggc ggaccgctat caggacatag cgttggctac ccgtgatatt gctgaagagc    2700
ttggcggcga atgggctgac cgcttcctcg tgctttacgg tatcgccgct cccgattcgc    2760
agcgcatcgc cttctatcgc cttcttgacg agttcttctg aggggatcaa ttctctagag    2820
ctcgctgatc agcctcgact gtgccttcta gttgccagcc atctgttgtt tgcccctccc    2880
ccgtgccttc cttgaccctg gaaggtgcca ctcccactgt cctttcctaa taaaatgagg    2940
aaattgcatc gcattgtctg agtaggtgtc attctattct ggggggtggg gtggggcagg    3000
acagcaaggg ggaggattgg gaagacaata gcaggcaaca acttcgtata atgtatgcta    3060
tacgaagtta tcagtacaag ccgaattctg cagatatcga aggaacaaat gcaacaatac    3120
tgaggttctc cagcattgtg cattcctttaa atggaatgca aagtaaagtg taattttcaa    3180
accaactaaa gcacttttag aaataataat aaaaaaacat gttactgtat ataaacctct    3240
aatgtataag gctttataga gaacacttta acaagaaatg tttcattttt agataccaga    3300
aatatgtaaa gtgaaaatcc tgattataga tttccttcac tatttagatg gagttatttt    3360
agggtacctg ggtttactta aaccaatata ggagtgccat gagtaagaaa tgtaattttg    3420
aattatgaca atgtatttaa gagaaagata gcttttttata cctgtaatct cactctgttc    3480
agtgtcaaaa ttaaagtata tattttagaa acagaaaaag caagaagtt atttaaaaga    3540 cgtaacttat ttaacttctt tgctcctgaa attcctcaag tataaaatga gaaggcaatg    3600
tagatgcact aaattagtct ctcccaaatt gtctccaata agaatcacct gcttcagaat    3660
gaatgcatta gtaggaatga agagggctgg aaatctgcat tttaacaaa tttttctactt    3720 aattcttatc aggcaagtct gggaagcatc agactagaag ttagtattgt attctatatt    3780
gcaactgact ttaatactcc tttaaataaa agtaccaaat acaatgaagc ccccctcac    3840 acatataatt tattaataaa ttcagccctc catcaagtat ccatcaattt ctattttctc    3900
tgtcatctac tctctctata caactgggcc aaaatgccag tgacatttac aaagaacttt    3960
gggaaaataa gatatctccc ttgttgttgt actcaaactg aatacatttt attttaattt    4020
gggaaggtat aattaatagt tgttattagt ttaaaccac tatttgatag atgttttaca    4080 cctgtttttct cattttgatt ctcctaataa tgacactaat aactaagcca gaagtctttta    4140 cagttttaca tcctatgctc tttctactac cgatgaggcc aatgaaagta aagaggtgaa    4200
atgtggtaga tggtgatgtt tatgaaaatt agttatctgc tatgcccttt gactgctgct    4260
ggatttctaa ggacatttgt atttagaaag gccaattttt tatcattctg tagtgcttct    4320
tttgtgaaga gatagggaaa taggccttgt gatttgagct caattgcttt tagtagtatt    4380
aaaataatgg gaaaaactta tgcaaacagt acatatatat tttgagaatt ttctcccctc    4440
tatattgaga aattggagga gctaactttt aacaaatttt ccacatttat aaactgtgat    4500
t                                                                      4501

<210> SEQ ID NO 2
```

```
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
gttccttcct cgagct                                                       16

<210> SEQ ID NO 3
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
tcggtacctt acattcc                                                      17
```